US007423027B2

(12) United States Patent
Lai et al.

(10) Patent No.: US 7,423,027 B2
(45) Date of Patent: Sep. 9, 2008

(54) METHODS OF USING GAMMA CYCLODEXTRIN TO CONTROL BLOOD GLUCOSE AND INSULIN SECRETION

(75) Inventors: Chron-Si Lai, Blacklick, OH (US); JoMay Chow, Gahanna, OH (US); Bryan W. Wolf, Ovalle (CL)

(73) Assignee: Abbott Laboratories, Abbott Park, IL (US)

( * ) Notice: Subject to any disclaimer, the term of this patent is extended or adjusted under 35 U.S.C. 154(b) by 385 days.

(21) Appl. No.: 11/062,243

(22) Filed: Feb. 18, 2005

(65) Prior Publication Data

US 2005/0215523 A1    Sep. 29, 2005

Related U.S. Application Data

(60) Provisional application No. 60/545,804, filed on Feb. 19, 2004.

(51) Int. Cl.
*A01N 43/04* (2006.01)
*A61K 31/715* (2006.01)
*C08B 37/16* (2006.01)

(52) U.S. Cl. ......................................... 514/58; 536/103
(58) Field of Classification Search ........................ None
See application file for complete search history.

(56) References Cited

U.S. PATENT DOCUMENTS

| 4,910,137 | A | 3/1990 | Kobayashi et al. |
| 5,189,149 | A | 2/1993 | Bruzzese et al. |
| 2003/0118712 | A1 | 6/2003 | Koren et al. |

FOREIGN PATENT DOCUMENTS

| JP | 57146713 | 9/1982 |
| JP | 62265230 | 11/1987 |
| JP | 3112932 | 5/1991 |
| JP | 7184597 | 7/1995 |

OTHER PUBLICATIONS

Nutrition Facts and Analysis for Yogurt, plain, whole milk. From http://www. NutritionData.com.*
Fact sheet Impaired Glucose Tolerance (IGT), International Diabetes Federation, from http://www.idf.org.*
Mayer-David. Diabetes Care, vol. 24, No. 4, Apr. 2001.*
Hayes. Diabetes Spectrum, vol. 15, No. 1, 2002, pp. 11-14.*
Dinsmoor, (www.DiabetesSelfManagement.com, Nighttime Hypo[oglycemia).*
"Gamma Cyclodextrin as a Novel Food Ingredient/Food Additive," Application A438, Draft Assessment Report, Food Standards Australia/New Zealand, Oct. 9, 2002.
"Gamma Cyclodextrin as a Novel Food Ingredient/Food Additive," Application A438, Final Assessment Report, Good Standards Australia/New Zealand, Mar. 19, 2003.
"In vitro action of human and porcine a-amylases on cyclomaltooligosacharides," Hitoshi Kondo, Hiroshi Nakatani and Keitaro Hiromi, Carbohydrate Research, 204 (1990) 207-213.
"Subchronic Oral Toxicity Studies with y-Cyclodextrin in Rats," B. Lina and A. Bar, Regulatory Toxicology and Pharmacology 27, 178-188 (1998). Article No. RT981223.
"Subchronic (13-week) Oral Toxicity Studies of y-Cyclodextrin in Dogs," H.P. Til and A. Bar, Regulatory Toxicology and Pharmacology 27, 159-165 (1998). Article No. RT981220.
Evaluation of Certain Food Additives and Contaminants, World Health Organization, Geneva 2000, Technical Report Series No. 896.
Evaluation of Certain Food Additives and Contaminants, World Health Organization, Geneva 2000, Technical Report Series No. 891.
"Embryotoxicity and Teratogenicity Study with y-Cyclodextrin in Rabbits," D.H. Waalkens-Berendsen, A.E. Smits-van Prooije and A. Bar, Regulatory Toxicology and Pharmacology 27, 172-177 (1998), Article No. RT981222.
Safety Evaluation of Certain Food Additives and Contaminants, World Health Organization, Food Additives Series #44, Report Series No. 969.
FDA Agency Response Letter GRAS Notice No. GRN 000046, Sep. 22, 2000.
Safety Evaluation of Certain Food Additives and Contaminants, World Health Organization, Food Additives Series #42, Report Series No. 937.
"Gastrointestinal tolerance of y-cyclodextrin in humans", Food Additives and Contaminants, 1999, vol. 16, No. 7, 313-317.
Parent Cyclodextrins, Cyclodextrins, Wacker-Chemie GmbH, www.wacker.com May 5, 2005.
The Cyclodextrin Expert, BL Biotechnology/Wacker-Chemie, Jan. 2000.
Alpha-cyclodextrin, Beta-cyclodextrin and Gamma-cyclodextrin, http://legalminds.lp.findlaw.com.
"Effects of Cooking on Serum Glucose and Insulin Responses to Starch," Short Reports from British Medical Journal, vol. 282, p. 1032, Mar. 28, 1981.
Gamma-Cyclodextrin, Monographs, Food Chemicals Codex, Dec. 31, 2001.

(Continued)

*Primary Examiner*—Shaojia Anna Jiang
*Assistant Examiner*—Layla Bland
(74) *Attorney, Agent, or Firm*—William J. Winter; Sandra E. Weida; Thomas D. Brainard

(57) ABSTRACT

Disclosed are methods of producing a blunted postprandial glycemic response in an individual, and/or reducing postprandial insulin secretion, said methods comprising administering to the individual a nutritional or other product comprising gamma-cyclodextrin. Also disclosed are similar other methods directed toward the use of such products to provide weight and appetite control, to normalize blood glucose levels in individuals with impaired glucose tolerance, to minimize nighttime hypoglycemia in diabetic and non-diabetic patients, to prevent reactive hypoglycemia in susceptible non-diabetics, to normalize blood glucose levels in individuals with gestational diabetes or impaired glucose tolerance during gestation, and/or to provide a prolonged glycemic response during exercise. The methods are based upon the discovery that gamma-cyclodextrins are rapidly metabolized and absorbed in the small intestine, but subsequently result in a surprisingly blunted postprandial glycemic response and reduced insulin secretion.

40 Claims, 7 Drawing Sheets

OTHER PUBLICATIONS

Draft CAVAMAX® W8 Food, Wacker Specialties, pp. 1/2.

"Supplemental Fructose Attenuates Postprandial Glycemia in Zucker Fatty *fa/fa* Rats" Bryan W. Wolf, Phillip M. Humphrey, Craig Hadley, Kati Maharry, Keith A. Garleb and Jeffrey Firkins, Nutrient Metabolism, American Society for Nutritional Sciences 2002, p. 1219-1223.

"Industrial Applications of Cyclodextrins," Inclusion Compounds, vol. 3, 1984, p. 330-390.

Chapter 5, "The Metabolism, Toxicity and Biological Effects of Cyclodextrins," CD's and Their Industrial Uses, D. Duchane, ED. Editions de Sante'—Paris 1987, p. 172-210.

"Nutritional Significance of Cyclodextrins: Indigestibility and Hypolipemic Effect of $\alpha$-Cyclodextrine," Masashige Suzuki, et al. J. Nutr. Sci. Vitaminol., 31, 209-223, 1985.

* cited by examiner

METHODS OF USING GAMMA CYCLODEXTRIN TO CONTROL BLOOD GLUCOSE AND INSULIN SECRETION (This application is related to provisional application U.S. Ser. No. 60/545,804 filed Feb. 19, 2004)

The present invention relates to methods of controlling postprandial blood glucose concentrations and insulin secretion in a diabetic or other individual using nutritional products containing γ-cyclodextrin.

BACKGROUND OF THE INVENTION

Cyclodextrins are well known ingredients for use in a variety of consumer products. Cyclodextrins are synthetic carbohydrates prepared from hydrolyzed starch by the action of cyclodextrin-glycosyl transferase, an enzyme obtainable from several organisms such as *Bacillus macerans* or related *Bacillus* strains. Cyclodextrins have a cyclic malto-oligosaccharide structure with 6 or more alpha-1,4-linked glucose units, the most common of which are alpha-cyclodextrin, beta-cyclodextrin, and gamma-cyclodextrin with 6, 7, and 8 linked glucose units, respectively.

Gamma-cyclodextrin, for example, can be characterized in terms of the following general structure:

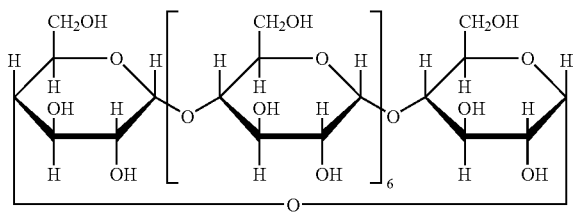

Due to its unique structure, gamma-cyclodextrin is often used in pharmaceutical and nutritional products as a delivery vehicle for hydrophobic or poorly water-soluble molecules. The hydrophobic inner core of the cyclodextrin molecule complexes with organic or otherwise compatible molecules, while the hydrophophilic outer surface of the cyclodextrin molecule allows for the entire inclusion complex to dissolve in an aqueous medium. This application of the cyclodextrin inclusion complex has been found especially useful in protecting sensitive molecules such as vitamins, flavorants, and similar other materials from oxidation, evaporation, or other forms of degradation, as formulated into a variety of nutritional products.

Gamma-cyclodextrins are frequently described in the literature as being a rapidly digested carbohydrate, unlike their alpha and beta counterparts which are generally recognized as non-digestible. The rapidly digested gamma-cyclodextrin has been characterized as such based upon a number of studies, including in vitro incubations with human salivary and pancreatic amylases (Kondo H, Nakatani H, Hiromi K: In vitro action of human porcine α-anlyases on cyclo-malto-oligosaccharides, Carbohydrate Research 1990; 204:207-213) and good tolerance of single 8 g doses when fed to healthy adult subjects (Koutsou G A, Storey D M, Bar A: Gastrointestinal tolerance of cyclodextrins in humans, Food Add Contamin 1999; 16:313-317). It has thus been assumed that gamma-cyclodextrin is completely degraded in the human small intestine (Wacker Bicochem Corp., Digestion of parent cyclodextrins, Jan. 17, 2000).

It has now been found, however, that orally administered gamma-cyclodextrin results in a surprisingly blunted blood glucose curve in both human and animal models. This is especially surprising given that the literature reports gamma-cyclodextrin as rapidly digested and absorbed in the small intestine, which would then be expected to result in a relatively steep blood glucose spike following administration. On the contrary, we found that gamma-cyclodextrin provides a blunted postprandial glucose response, as well as reduced insulin secretion, more akin to that of a slowly digested carbohydrate rather than the rapidly digested carbohydrate that gamma-cyclodextrin has been reported in the literature to be. These new findings are based primarily upon a study involving male fatty Zucker fa/fa rats fed gamma cyclodextrin compared with a maltodextrin challenge, and a human study of healthy non-diabetic human subjects which corroborated the observations made in the rat study. Both studies are described hereinafter in greater detail.

It has also been found, based primarily upon the above-referenced data, that nutritional products can be formulated with gamma-cyclodextrin to provide diabetics or other suitable individuals with a nutrition source that delivers a blunted postprandial glycemic response. These products allow for better control over blood glucose fluctuations, both hyper- and hypoglycemic swings, after eating a meal or snack. This is especially useful in individuals prone to such glycemic swings, including those afflicted with various degrees of glucose intolerance such as insulin-dependent diabetes mellitus (IDDM) and non-insulin dependent diabetes mellitus (NIDDM).

It has also been found that the above-referenced products are useful in most any application where control of postprandial blood glucose is desirable, such as to control appetite by way of blood glucose control as described herein, and subsequent control over body weight management.

It is therefore an object of the present invention to provide a method of providing nutrition that also provides blood glucose control following administration of the nutrition. It is a further object of the present invention to provide diabetics or others with a method of obtaining nutrition and better postprandial blood glucose control. It is a further object of the present invention to provide a method of controlling appetite and managing body weight, by administering nutritional products that deliver a blunted blood glucose response following such administration. It is yet another object of the present invention to provide such methods using gamma-cyclodextrin, and further to provide such benefits through the administration of nutritional products containing gamma-cyclodextrin.

SUMMARY OF THE INVENTION

The present invention is directed to a method of producing a blunted glycemic response in an individual, said method comprising administering to the individual a nutritional product comprising gamma-cyclodextrin, preferably at least about 1% gamma-cyclodextrin for solid product forms and at least about 0.1% for liquid product forms, all by weight of the selected product form.

The present invention is also directed to a method of providing an individual with nutrition while reducing appetite, said method comprising administering to the individual a nutritional product comprising γ-cyclodextrin, preferably at least about 1% gamma-cyclodextrin for solid product forms and at least about 0.1% for liquid product forms, all by weight of the selected product form.

The present invention is also directed to a method of providing an individual with nutrition while reducing total body weight, said method comprising administering to the individual a nutritional product comprising γ-cyclodextrin, preferably at least about 1% gamma-cyclodextrin for solid product forms and at least about 0.1% for liquid product forms, all by weight of the selected product form.

The present invention is also directed to a method of providing an individual with nutrition while controlling insulin secretion, said method comprising administering to the individual a nutritional product comprising γ-cyclodextrin, preferably at least about 1% gamma-cyclodextrin for solid product forms and at least about 0.1% for liquid product forms, all by weight of the selected product form.

The present invention is also directed to a number of other methods of providing an individual with nutrition while controlling postprandial blood glucose concentrations under a variety of circumstances, including 1) method of normalizing blood glucose levels in individuals with impaired glucose tolerance, 2) method of preventing nighttime hypoglycemia in diabetic patients, 3) method of preventing reactive hypoglycemia for those individuals who are not diabetic but are prone to hypoglycemic swings, 4) a method of normalizing blood glucose levels in individuals with gestational diabetes or impaired glucose tolerance during gestation, and 5) a method of providing a prolonged glycemic response and sustained energy release during exercise, especially prolonged exercise. All such methods are preferably directed to the oral administration of a nutritional product containing gamma-cyclodextrin as described herein prior to the circumstance unique to that method, e.g., prior to bedtime for preventing nighttime hypoglycemia, e.g., prior to or during exercise to provide a prolonged glycemic response during exercise, etc.

It has now been found that orally administered gamma-cyclodextrin results in a surprisingly blunted postprandial blood glucose response, and a corresponding reduction in insulin secretion. This blunted glycemic response was unexpected in view of current literature that teaches gamma-cyclodextrin is rapidly digested and absorbed in the small intestine. One would have expected such a rapidly digested and absorbed carbohydrate to produce a relatively sharp postprandial blood glucose spike, not the blunted glycemic response discovered in both the animal and human studies described herein.

The methods of the present invention are therefore based upon the discovery that orally administered gamma-cyclodextrin delivers a surprisingly blunted postprandial glycemic response, and reduced insulin secretion. The methods of the present invention are therefore directed to those individuals in whom such a response would be beneficial, especially diabetics or other individuals with different degrees of glucose intolerance. These methods are also useful in controlling appetite, and ultimately weight gain, since there is a correlation between appetite and control of blood glucose levels and insulin secretion. All such methods are therefore directed to the administration of gamma-cyclodextrin or nutritional products containing gamma-cyclodextrin to achieve the blunted postprandial glycemic response described herein, for conditions directly or indirectly responsive to such a blunted glycemic response, e.g., insulin intolerance or diabetes mellitus, appetite control and body weight management.

DETAILED DESCRIPTION OF THE INVENTION

Figure 1:
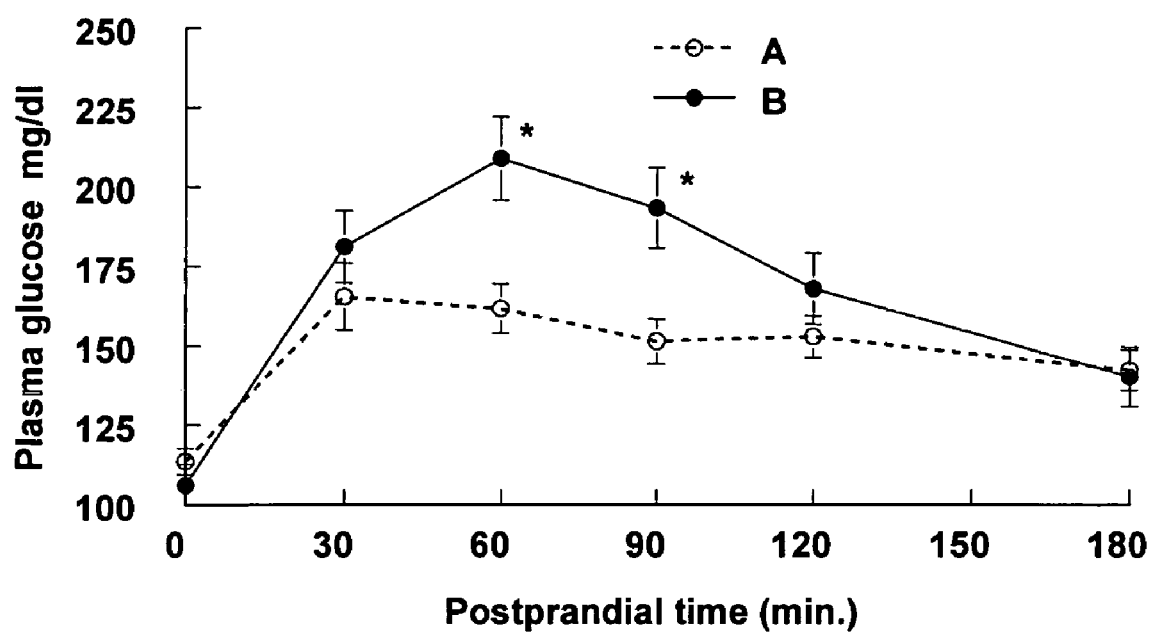
FIG. 1 is a graph illustrating the postprandial plasma glucose response of 20 male Zucker fa/fa rats as part of the animal study described hereinafter, wherein the rats are challenged with gamma-cyclodextrin (A) or Lodex 15, maltodexrin (B).

The methods of the present invention comprise administration of nutritional products containing gamma-cyclodextrin, for uses in various individuals who would benefit from the resulting blunted glycemic response and insulin secretion. These and other essential elements or limitations of the methods of the present invention are described in detail hereinafter.

The term "blunted glycemic response" as used herein, unless otherwise specified, refers to a reduction in the peak blood glucose response in an individual after oral administration of gamma-cyclodextrin as compared to the peak glycemic response from an weight equivalent dose of Lodex 15®, a maltodextrin with a dextrose equivalence of 15, available from Cerestar U.S.A., Indianapolis, Ind.

The term "hypoglycemia" refers to a decrease in the plasma glucose concentration to a level sufficient to produce symptoms, with attenuation of symptoms upon restoration of normal glucose concentration.

The term "slowly digested carbohydrate" as used herein, unless otherwise specified, refers to a carbohydrate that has a slow rate of digestion, in which the gold standard is raw cornstarch, and more specifically has a rate of digestion that is slower than hydrolyzed cornstarch, (for example Lodex 15® from Cerester).

The term "rapidly digested carbohydrate" as used herein, unless otherwise specified, refers to a carbohydrate that is rapidly digested, e.g. unmodified maltodextrin (for example Lodex 15® from Cerester) and is digested at a rate equal to or faster than an unmodified maltodextrin, such as Lodex 15®.

The term "lipid" as used herein, unless otherwise specified, means fats, oils, and combinations thereof.

The term "meal replacement product" as used herein, unless otherwise specified, includes any nutritional product containing protein, carbohydrate, lipid, vitamins and minerals, the combination of which is then suitable as a sole or primary nutrition source for a meal.

The term "nutritional product" as used herein, unless otherwise specified, the gamma-cyclodextrin products described herein containing one or more of protein, additional carbohydrate, or lipid nutrients, and includes but is not limited to meal replacement products.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the invention described herein, as well as any additional or optional ingredients, components, or limitations described herein or otherwise useful in a nutritional applications.

Product Form

The methods of the present invention are directed to the administration of gamma-cyclodextrin in any product form suitable for oral administration, non-limiting examples of which include dietary supplements, pharmaceutical dosage forms, nutritional products, or any other known or otherwise effective form of oral delivery.

The methods of the present invention are preferably directed to the oral administration of nutritional products or food supplements, to thus control the blood glucose response secondary to the administration of such products. Non-limiting examples of suitable nutritional products for use in the methods of the present invention include liquid beverages, nutritional solids (e.g., snack or meal bars, powders, gels, breakfast cereals, baked goods, candy, etc.), frozen solids (e.g., frozen shakes, popsicles, etc.), and the like.

The methods of the present invention are also directed to the oral administration of gamma-cyclodextrin in dosage forms such as capsules, tablets, caplets, pills, and liquid dosage forms such as solutions, suspensions or emulsions, liquid gels, and so forth. Such dosage forms most typically contain one or more excipients for effective formulation of the desired dosage form.

The methods of the present invention are preferably directed to the oral administration of nutritional products containing gamma-cyclodextrin, especially products in the form of liquid beverages or in the form of nutritional bars. In such embodiments of the present invention, the gamma-cyclodextrin can be incorporated into any of a variety of meal replacement beverages such as those available from Ross Products Division, Abbott Laboratories, Columbus, Ohio, USA, such as Glucerna® Shake, Ensure® Liquid Nutrition, Pediasure®, Osmolite® Liquid Nutrition, Enlive® Clear Liquid Nutrition, Jevity® Liquid Nutrition, Nepro® Balanced Nutrition, Optimental® Ready to Feed Elemental, Promote® Liquid Nutrition, Pulmocare®, or any other suitable Ross nutritional product.

The methods are also directed to product forms including sports drinks or other electrolyte replacement product, especially as such products are used prior to, during, and/or after exercise, especially prolonged or vigorous exercise. Examples of such product forms include those such as Gatorade® brand beverages (available from Pepsi Co., Inc, Purchase, N.Y.), Powerade® brand beverages (available from The Coca-Cola Company) and Sunny Delight® brand beverages (available from The Procter & Gamble Company, Cincinnati, Ohio), wherein such product forms are modified by an appropriate amount of gamma-cyclodextrin as described herein.

The method of the present invention is also preferably directed to the oral administration of gamma-cyclodextrin in a nutritional bar product form, including both snack and meal replacement bars. In such embodiments of the present invention, the gamma-cyclodextrin can be incorporated into any of a variety of meal replacement bars such as those available from Ross Products Division, Abbott Laboratories, Columbus, Ohio, USA, such as Ensure® Nutrition Bars, Glucema® Snack Bars, ZonePerfect® Bars, and other Ross solid nutritional products. Other suitable meal replacement bars suitable for incorporation of gamma-cyclodextrin include Slim Fast® Bars (available from Slim Fast Foods Company, West Palm Beach, Fla., Gatorade® brand bars (available from Pepsi Co., Inc, Purchase, N.Y.), or any other commercially available or otherwise known nutritional snack or meal replacement solid.

For methods directed to liquid beverages, gamma-cyclodextrin concentrations in such beverages are generally at least about 0.1%, including from about 0.5% to about 10%, also including from about 1% to about 6%, and also including form about 1% to about 4%, and also including form about 2% to about 3%, by weight of the liquid beverage.

For methods directed to solid product forms, especially nutritional bars, gamma-cyclodextrin concentrations are generally at least about 1%, including from about 2% to about 20%, also including from about 3% to about 12%, and also including form about 5% to about 11%, and also including form about 6% to about 9%, by weight of the solid product form.

In any of the product forms described or otherwise suggested herein for use in the method, the gamma cyclodextrin can be formulated into the product by simply adding it to the other nutrients or additives or by replacing some or all of the other carbohydrates or other nutrients or excipients in the product. The gamma-cyclodextrin may represent up to 100% of the carbohydrates in the product form, including from about 5% to about 90%, and also including from about 6% to about 50%, and also including from about 10% to about 30%, and also including from about 12% to about 25%, by weight of the total carbohydrates in the product.

The resulting carbohydrate blend in the product form can be selected or otherwise adjusted by one of ordinary skill in the nutrition formulation art so as to provide the desired postprandial blood glucose profile in the targeted user.

Gamma-cyclodextrin

The gamma-cyclodextrin suitable for use in the methods of the present invention includes any source of gamma-cyclodextrin or substituted gamma-cyclodextrin, provided that the source is safe for oral administration in humans in the selected product form.

Gamma-cyclodextrin (γ-cyclodextrin; gamma-CD; cyclooctaamylose; cyclomaltooctaose) is a non-reducing cyclic saccharide having eight 1,4-linked D-glucopyranosyl units manufactured by the action of cyclomaltodextrin glucanotransferase on hydrolyzed starch followed by purification of the gamma-cyclodextrin. It is generally available as a white or almost-white crystalline solid that is freely soluble in water. It is most often used in food products as a stabilizer, emulsifier, carrier, or as some other formulation aid.

The gamma-cyclodextrin suitable for use herein is therefore a cyclic oligosaccharide well known in the various chemical and nutrition arts. The gamma-cyclodextrin may be substituted or unsubstituted, and includes alkylated, acylated, hydroxylated, or other known or otherwise suitable derivatives, non-limiting examples of which include hydroxypropyl gamma cyclodextrin, quaternary ammonium gamma cyclodextrin, carboxymethyl gamma cyclodextrin, carboxyethyl gamma cyclodextrin, hydroxyethyl gamma cyclodextrin, and combinations thereof. Unsubstituted gamma-cyclodextrin is preferred.

The gamma-cyclodextrin can be formulated along with other ingredients, including other ingredients complexed to the cyclodextrin ring to form a protected inclusion complex. The latter is especially useful for inclusion of some bitter tasting ingredients as well as volatile or degradation sensitive materials such as flavors and some vitamins. The nutritional products for use in the methods of the present invention are, however, preferably substantially free of alpha-cyclodextrin, beta-cyclodextrin, or both. In this context, "substantially free" means that the products preferably contain less than about 0.5%, more preferably less than about 0.1%, more preferably zero percent, of the alpha and beta cyclodextrins.

A non-limiting example of a commercially available gamma-cyclodextrin suitable for use herein includes Cavamax® W8 Food (gamma-cyclodextrin powder) available from Wacker-Chemie GmbH, Germany.

Nutrients

The methods of present invention are preferably directed to the use of nutritional product forms containing sufficient types and amounts of nutrients to meet the targeted needs of the intended user. These nutritional product forms may therefore comprise, in addition to the gamma-cyclodextrin, protein, additional carbohydrate, lipid, or combinations thereof. The nutritional products may also further comprise vitamins, minerals or other nutritious ingredients suitable for use in an oral nutritional product.

Many different sources and types of carbohydrates, lipids, proteins, minerals and vitamins are known and can be used in the nutritional product forms described herein, provided that the selected nutrients are compatible with the added ingredients in the chosen product form, are safe and effective for their intended use, and do not otherwise unduly impair product performance.

Carbohydrates suitable for use in the nutritional products can be simple, complex, or variations or combinations thereof. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, indigestible oligosaccharides (e.g., fructooligosaccharides), honey, sugar alcohols (e.g., maltitol, erythritol, sorbitol), and combinations thereof.

Carbohydrates suitable for use herein also include soluble dietary fiber, non-limiting examples of which include gum arabic, sodium carboxymethyl cellulose, guar gum, citrus pectin, low and high methoxy pectin, oat and barley glucans, carrageenan, psyllium and combinations thereof. Soluble dietary fiber is also suitable as a carbohydrate source herein, non-limiting examples of which include oat hull fiber, pea hull fiber, soy hull fiber, soy cotyledon fiber, sugar beet fiber, cellulose, corn bran, and combinations thereof.

Proteins suitable for use in the nutritional products include, but are not limited to, hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. The proteins for use herein can also include, or be entirely or partially replaced by, free amino acids known for use in nutritional products, non-limiting examples of which include tryptophan, glutamine, tyrosine, methionine, cysteine, arginine, and combinations thereof.

Lipids suitable for use in the nutritional products include, but are not limited to, coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, flax seed oil, and combinations thereof.

Concentration or amounts of carbohydrate, protein, and carbohydrate in the nutritional product forms can vary considerably depending upon the particular product and formulation needs. These macro-nutrients are most typically formulated within any of the ranges described in the following table.

| Nutrient* | Nutrient Ranges | | | | | |
|---|---|---|---|---|---|---|
| | Nutritional Solid | | | Nutritional Liquid Beverage | | |
| Carbohydrate | 0-100 | 5-80 | 35-70 | 0-100 | 5-75 | 35-70 |
| % total calories | | 25-75 | | | 25-75 | |
| Lipid | 0-40 | 5-35 | 10-30 | 0-40 | 5-35 | 10-30 |
| % total calories | | | | | | |

-continued

| Nutrient* | Nutrient Ranges | | | | | |
|---|---|---|---|---|---|---|
| | Nutritional Solid | | | Nutritional Liquid Beverage | | |
| Protein % total calories | 0-100 | 5-40<br>5-35<br>10-35 | 15-25 | 0-100 | 5-40<br>5-35<br>10-35 | 15-25 |
| Gamma-cyclodextrin wt/wt % based on total product weight | ≧1 | 2-20<br>3-12<br>5-11 | 6-9 | ≧0.1 | 0.5-10<br>1-6<br>1-4 | 2-3 |

*each numerical value is preceded by the term "about"

The nutritional products may further comprise any of a variety of vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional products may further comprise any of a variety of minerals, non-limiting examples of which include calcium, phosphorus, magnesium, iron, zinc, manganese, copper, iodine, sodium, potassium, molybdenum, selenium, chromium, chloride, and combinations thereof.

Optional Ingredients

The nutritional product forms of the present invention may further comprise other optional components that may modify the physical, chemical, aesthetic or processing characteristics of the products or serve as pharmaceutical or additional nutritional components when used in the targeted population. Many such optional ingredients are known or otherwise suitable for use in food and nutritional products and may also be used in the nutritional product forms herein, provided that such optional materials are compatible with the ingredients and product form selected, are safe and effective for their intended use, and do not otherwise unduly impair product performance.

Non-limiting examples of such optional ingredients include preservatives, anti-oxidants, emulsifying agents, buffers, artificial sweeteners (e.g., saccharine, aspartame, acesulfame K, sucralose) colorants, flavors, thickening agents and stabilizers, emulsifying agents, lubricants, and so forth.

Methods of Use

The methods of the present invention include those embodiments directed to producing a blunted glycemic response in an individual, said method comprising administering to the individual a nutritional product comprising gamma-cyclodextrin, preferably at least about 1% gamma-cyclodextrin for solid product forms and at least about 0.1% for liquid product forms, all by weight of the selected product form. The method may further comprise those embodiments directed to the various nutritional products described herein.

The present invention is also directed to a method of providing an individual with nutrition while reducing appetite, said method comprising administering to the individual a nutritional product comprising gamma-cyclodextrin, preferably at least about 1% gamma-cyclodextrin for solid product forms and at least about 0.1% for liquid product forms, all by weight of the selected product form. The method may further comprise those embodiments directed to the various nutritional products described herein.

The present invention is also directed to a method of providing an individual with nutrition while reducing total body weight, said method comprising administering to the individual a nutritional product comprising gamma-cyclodextrin, preferably at least about 1% gamma-cyclodextrin for solid product forms and at least about 0.1% for liquid product forms, all by weight of the selected product form. The method may further comprise those embodiments directed to the various nutritional products described herein.

The present invention is also directed to a method of providing an individual with nutrition while controlling insulin secretion, said method comprising administering to the individual a nutritional product comprising gamma-cyclodextrin, preferably at least about 1% gamma-cyclodextrin for solid product forms and at least about 0.1% for liquid product forms, all by weight of the selected product form. The method may further comprise those embodiments directed to the various nutritional products described herein.

Each of the above-described methods of the present invention include those embodiments directed to the various nutritional products as described herein, and are especially useful when applied to individuals afflicted with diabetes mellitus, either IDDM or NIDDM, or other forms of glucose intolerance. The methods are preferably directed to nutritional products with sufficient nutrients to be a meal replacement product.

The methods of the present invention are also directed to a number of other methods of providing an individual with nutrition while controlling postprandial blood glucose concentrations under a variety of circumstances, including 1) method of normalizing blood glucose levels in individuals with impaired glucose tolerance, 2) method of preventing nighttime hypoglycemia in diabetic patients, 3) method of preventing reactive hypoglycemia for those individuals who are not diabetic but are prone to hypoglycemic swings, 4) a method of normalizing blood glucose levels in individuals with gestational diabetes or impaired glucose tolerance during gestation, and 5) a method of providing a prolonged glycemic response during exercise, especially prolonged exercise. All such methods are preferably directed to the oral administration of a nutritional product containing gamma-cyclodextrin as described herein prior to the circumstance unique to that method, e.g., prior to bedtime for preventing nighttime hypoglycemia, e.g., prior to or during exercise to provide a prolonged glycemic response during exercise, etc.

Manufacture

The nutritional products for use in the methods of the present invention can be prepared by any known or otherwise effective manufacturing technique for preparing the selected product form. Many such techniques are known for any given product form such as nutritional beverages or nutritional bars and can easily be applied by one of ordinary skill in the art to the nutritional products described herein.

Liquid meal replacement beverages, for example, can be prepared by first forming an oil and fiber blend containing all oils, any emulsifier, fiber and the fat soluble vitamins. Three more slurries (carbohydrate and two protein) are prepared separately by mixing the carbohydrate and minerals together and the protein in water. The slurries are then mixed together with the oil blend. The resulting mixture is homogenized, heat processed, standardized with water-soluble vitamins, flavored and the liquid terminally sterilized or dried to produce a powder.

In yet another example, solid nutritional bars may be manufactured using cold extrusion technology as is known and commonly practiced in the bar manufacturing art. To prepare such compositions, typically all of the powdered components are dry blended together, which typically includes the proteins, vitamin premixes, certain carbohydrates, etc. The fat soluble components are then blended together and mixed with any powdered premixes. Finally any liquid components are then mixed into the composition, forming a plastic like composition or dough. The resulting plastic mass can then be shaped, without further physical or chemical changes occurring, by cold forming or extrusion, wherein the plastic mass is forced at relatively low pressure through a die, which confers the desired shape. The resultant exudate is then cut off at an appropriate position to give products of the desired weight. If desired the solid product is then coated, to enhance palatability, and packaged for distribution.

The solid nutritional product forms for use in the methods of the present invention may also be manufactured through a baked application or heated extrusion to produce solid product forms such as cereals, cookies, crackers, and similar other solid forms. One knowledgeable in the nutrition manufacturing arts is able to select one of the many known or otherwise available manufacturing processes to produce the desired final product.

Gamma-cyclodextrin may also be incorporated into a variety of different liquid beverages, non-limiting examples of which include juices, carbonated and non-carbonated beverages, flavored waters, electrolyte-containing sports drinks, and so forth. The gamma-cyclodextrin may be formulated into the composition in the same manner that most any carbohydrate source, especially water soluble carbohydrates, are formulated into such beverages. For example, the beverage carbohydrate, including gamma-cyclodextrin, is dissolved in an appropriate volume of water. Flavors, colors, vitamins, and other suitable ingredients are then optionally added to the aqueous mixture, which is then pasteurized, packaged and stored until shipment.

The nutritional product forms for use in the methods of the present invention may, of course, be manufactured by other known or otherwise suitable techniques not specifically described herein without departing from the spirit and scope of method of the present invention. The present embodiments are, therefore, to be considered in all respects as illustrative and not restrictive and that all changes and equivalents also come within the description of the present invention. The following non-limiting examples will further illustrate the method of the present invention and some of the nutritional products suitable for use therein.

EXAMPLES

The following examples illustrate specific embodiments of the methods of the present invention, including some nutritional products for use in those methods and the techniques used to prepare those products. The examples are given solely for the purpose of illustration and are not to be construed as limitations of the present invention, as many variations thereof are possible without departing from the spirit and scope of the invention.

Each of the exemplified products described hereinafter is used in accordance with each of the methods of the present invention. The products described in Examples 1, 2, and 4 are used as meal replacement products (50 g nutritional bar or 8 fl. oz. of nutritional liquid) in selected individuals. The fortified juice products of Example 3 are used as a carbohydrate source (8 fl. oz.).

Each exemplified product is therefore specifically applied to each of the following methods of the present invention:

1. Orally administer to diabetic and non-diabetic individuals resulting in a blunted glycemic response in those individuals.
2. Orally administer to individuals with a subsequent appetite reduction to assist in a weight reduction program.
3. Orally administered to individuals with a subsequent reduction in peak serum insulin concentrations or AUC.
4. Orally administered to individuals with impaired glucose tolerance with subsequent normalization or improved normalization of postprandial blood glucose levels.
5. Orally administered to diabetic individuals, IDDM and NIDDM, at bedtime with a subsequent reduction in the occurrence of nighttime hypoglycemia.
6. Orally administered to non-diabetic individuals prone to hypoglycemic swings, with a subsequent improvement in postprandial blood glucose normalization.
7. Orally administered to individuals with gestational diabetes or impaired glucose tolerance during pregnancy, with a subsequent improvement in blood glucose normalization.
8. Orally administered to an individual within 30 minutes of exercise, with a subsequent prolongation of the postprandial glycemic response during exercise.

Example 1

This example illustrates a method of the present invention directed to the use of a nutritional product in the form of a liquid beverage. The formula for each sample batch of the corresponding exemplified beverage is set forth in the following table. All ingredient amounts are listed as kg per 1000 kg batch of product.

EXAMPLE 1

Liquid Beverages

| | Example 1.1 | Example 1.2 | Example 1.3 | Example 1.4 | Example 1.5 | Example 1.6 |
|---|---|---|---|---|---|---|
| I. Carbohydrate/Mineral Solution | | | | | | |
| Water | 165.2 | 165.2 | 165.2 | 165.2 | 165.2 | 165.2 |
| UTM/TM Premix | 0.3693 | 0.3693 | 0.3693 | 0.3693 | 0.3693 | 0.3693 |
| K citrate | 1.24 | 1.24 | 1.24 | 1.24 | 1.24 | 1.24 |
| Na citrate | 1.44 | 1.44 | 1.44 | 1.44 | 1.44 | 1.44 |
| K chloride | 0.607 | 0.607 | 0.607 | 0.607 | 0.607 | 0.607 |
| Mg chloride | 2.18 | 2.18 | 2.18 | 2.18 | 2.18 | 2.18 |
| K phosphate dibasic | 0.70 | 0.70 | 0.70 | 0.70 | 0.70 | 0.70 |
| TCP | 2.8 | 2.8 | 2.8 | 2.8 | 2.8 | 2.8 |
| Gellan gum | 0.125 | 0.125 | 0.125 | 0.125 | 0.125 | 0.125 |
| Chromium chloride | 0.002249 | 0.002249 | 0.002249 | 0.002249 | 0.002249 | 0.002249 |
| Mg phosphate dibasic | 1.023 | 1.023 | 1.023 | 1.023 | 1.023 | 1.023 |
| K Iodide | 0.000198 | 0.000198 | 0.000198 | 0.000198 | 0.000198 | 0.000198 |
| Fructooligosaccharide | 4.60 | 4.60 | 4.60 | 4.60 | 4.60 | 4.60 |
| Maltitol syrup | 40.00 | 40.00 | 40.00 | 40.00 | 40.00 | 6.5 |
| Fructose | 26.9 | 26.9 | 26.9 | 26.9 | 26.9 | 26.9 |
| Maltodextrin | 44.5 | 41.5 | 36.5 | 26.5 | 0 | 0 |
| Gamma-cyclodextrin | 2.0 | 5.0 | 10.0 | 20.0 | 46.5 | 80.0 |
| Fibrim 300 | 3.75 | 3.75 | 3.75 | 3.75 | 3.75 | 3.75 |
| Fibersol | 8.00 | 8.00 | 8.00 | 8.00 | 8.00 | 8.00 |
| II. Fat Solution | | | | | | |
| Canola oil | 3.4 | 3.4 | 3.4 | 3.4 | 3.4 | 3.4 |
| HOSO | 28.90 | 28.90 | 28.90 | 28.90 | 28.90 | 28.90 |
| Soy lecithin | 1.7 | 1.7 | 1.7 | 1.7 | 1.7 | 1.7 |
| Vitamin A Palmitate | 0.00635 | 0.00635 | 0.00635 | 0.00635 | 0.00635 | 0.00635 |
| Vitamin E | 0.098985 | 0.098985 | 0.098985 | 0.098985 | 0.098985 | 0.098985 |
| Vitamin D, E, K premix | 0.0653 | 0.0653 | 0.0653 | 0.0653 | 0.0653 | 0.0653 |
| Viscarin SD389 | 0 | 0 | 0 | 0 | 0 | 0 |
| Beta carotene | 0.00891 | 0.00891 | 0.00891 | 0.00891 | 0.00891 | 0.00891 |
| Calcium caseinate | 5.6 | 5.6 | 5.6 | 5.6 | 5.6 | 5.6 |
| Fibrim 300 | 3.75 | 3.75 | 3.75 | 3.75 | 3.75 | 3.75 |
| Lutein | 0.06922 | 0.06922 | 0.06922 | 0.06922 | 0.06922 | 0.06922 |
| III. Protein Solution | | | | | | |
| Water | 415.00 | 415.00 | 415.00 | 415.00 | 415.00 | 415.00 |
| Sodium caseinate | 30.10 | 30.10 | 30.10 | 30.10 | 30.10 | 30.10 |
| Soy protein isolate | 8.7 | 8.7 | 8.7 | 8.7 | 8.7 | 8.7 |

The exemplified beverages are prepared by combining the carbohydrate/mineral ingredients with heat at 155° F. A separate protein solution is prepared with the protein solution ingredients with heat at 140° F., and a separate fat solution is prepared with the fat solution ingredients with heat at 120° F. The three formed solutions are then combined in a blend tank, and subjected to the following process steps:
- deaerate the mix at 10-15 inches of Hg
- using a positive pump, pump blend mix through a plate heater
- heat mix to 160-180° F.
- UHT treatment preheat mix to 208-220° F.
- Heat mix to 295°±2° F. (steam injection), hold time 5 seconds
- Flash cool mix to 208-220° F.
- Cool mix further to 160-170° F.
- Homogenize mix at 3900-4100/400-600 psig
- Hold mix at 165-185° F. for 16 seconds
- Cool the mix to 34-44° F.

The cooled mixture is standardized with water 213 lbs (estimated), ascorbic acid (0.584 lbs), acesulfame K (0.075 lbs), vitamin premix (0.09742 lbs), choline chloride (0.472 lbs), NA vanilla flavor 1.80 lbs, and acesufame K (0.0174 lbs). The standardized mix is then packaged and subjected to retort processing in 8 oz metal cans. The packaged liquid beverage is then used in accordance with the methods of the present invention as described hereinbefore.

Example 2

This example illustrates a method of the present invention directed to the use of other nutritional products in a liquid beverage form. Listed in the table below are several ingredient profiles for 1000 kg batches of the exemplified beverages. All ingredient amounts are listed as kg per 1000 kg of product.

EXAMPLE 2

Liquid Beverages

| Ingredient | Example 2.1 | Example 2.2 | Example 2.3 | Example 2.4 | Example 2.5 |
|---|---|---|---|---|---|
| Water | Q.S. | Q.S. | Q.S. | Q.S. | Q.S. |
| Maltodextrin M-100 | 48.300000 | 42.252000 | 32.252000 | 22.252000 | 0 |
| Maltitol Syrup | 33.070000 | 33.070000 | 33.070000 | 33.070000 | 33.070000 |

EXAMPLE 2-continued

Liquid Beverages

| Ingredient | Example 2.1 | Example 2.2 | Example 2.3 | Example 2.4 | Example 2.5 |
|---|---|---|---|---|---|
| Acid Casein | 29.429910 | 29.429910 | 29.429910 | 29.429910 | 29.429910 |
| Fructose | 26.900000 | 26.900000 | 26.900000 | 26.900000 | 26.900000 |
| Gamma Cyclodextrin | 3.952 | 10.0 | 20.0 | 30.0 | 48.3 |
| High Oleic Safflower Oil | 29.085000 | 29.085000 | 29.085000 | 29.085000 | 29.085000 |
| Soy Protein Isolate* | 8.7195200 | 8.7195200 | 8.7195200 | 8.7195200 | 8.7195200 |
| Fibersol 2 | 8.0200000 | 8.0200000 | 8.0200000 | 8.0200000 | 8.0200000 |
| Soy Fiber (Fibrim 300) | 7.4011000 | 7.4011000 | 7.4011000 | 7.4011000 | 7.4011000 |
| Calcium Caseinate | 5.5966600 | 5.5966600 | 5.5966600 | 5.5966600 | 5.5966600 |
| FOS | 4.6100000 | 4.6100000 | 4.6100000 | 4.6100000 | 4.6100000 |
| m-Tricalcium Phosphate | 2.8000000 | 2.8000000 | 2.8000000 | 2.8000000 | 2.8000000 |
| Magnesium Chloride | 2.2000000 | 2.2000000 | 2.2000000 | 2.2000000 | 2.2000000 |
| Vanilla Flavor | 1.8000441 | 1.8000441 | 1.8000441 | 1.8000441 | 1.8000441 |
| Canola Oil | 3.4218000 | 3.4218000 | 3.4218000 | 3.4218000 | 3.4218000 |
| Soy Lecithin | 1.7109000 | 1.7109000 | 1.7109000 | 1.7109000 | 1.7109000 |
| Sodium Citrate | 1.3580000 | 1.3580000 | 1.3580000 | 1.3580000 | 1.3580000 |
| Magnesium Phosphate Dibasic | 1.0280000 | 1.0280000 | 1.0280000 | 1.0280000 | 1.0280000 |
| Ascorbic Acid | 0.7884000 | 0.7884000 | 0.7884000 | 0.7884000 | 0.7884000 |
| Potassium Chloride | 0.8000000 | 0.8000000 | 0.8000000 | 0.8000000 | 0.8000000 |
| Potassium Phosphate Dibasic | 0.7000000 | 0.7000000 | 0.7000000 | 0.7000000 | 0.7000000 |
| Choline Chloride | 0.4720020 | 0.4720020 | 0.4720020 | 0.4720020 | 0.4720020 |
| UTM/TM Premix | 0.4407000 | 0.4407000 | 0.4407000 | 0.4407000 | 0.4407000 |
| Vitamin E | 0.0990080 | 0.0990080 | 0.0990080 | 0.0990080 | 0.0990080 |
| Water soluble vitamin premix | 0.0974210 | 0.0974210 | 0.0974210 | 0.0974210 | 0.0974210 |
| Gellan Gum | 0.0750000 | 0.0750000 | 0.0750000 | 0.0750000 | 0.0750000 |
| Acesulfame Potassium | 0.0749560 | 0.0749560 | 0.0749560 | 0.0749560 | 0.0749560 |
| Lutein, 5% in Corn Oil | 0.0692325 | 0.0692325 | 0.0692325 | 0.0692325 | 0.0692325 |
| Vitamins D, E, K premix | 0.0650353 | 0.0650353 | 0.0650353 | 0.0650353 | 0.0650353 |
| Beta-Carotene | 0.0089100 | 0.0089100 | 0.0089100 | 0.0089100 | 0.0089100 |
| Vitamin A | 0.0063475 | 0.0063475 | 0.0063475 | 0.0063475 | 0.0063475 |

*Supro 1610

The exemplified beverages are prepared in accordance with the process described in Example 1. The liquid beverage is prepared by combining the carbohydrate/mineral ingredients with heat at 155° F. A separate protein solution is prepared with the protein solution ingredients with heat at 140° F., and a separate fat solution is prepared with heat at 120° F. The three formed solutions are then combined in a blend tank, and subjected to the following process steps:

- deaerate the mix at 10-15 inches of Hg
- using a positive pump, pump blend mix through a plate heater
- heat mix to 160-180° F.
- UHT treatment preheat mix to 208-220° F.
- Heat mix to 295°±2° F. (steam injection), hold time 5 seconds
- Flash cool mix to 208-220° F.
- Cool mix further to 160-170° F.
- Homogenize mix at 3900-4100/400-600 psig
- Hold mix at 165-185° F. for 16 seconds
- Cool the mix to 34-44° F.

The cooled mixture is standardized and then packaged and subjected to retort processing in 8 oz metal cans. The packaged liquid beverage is then used in accordance with the methods of the present invention as described hereinbefore.

Example 3

This example illustrates a method of the present invention directed to the use of a nutritional product in the form of a fortified juice drink. Listed in the table below are ingredient profiles for sample batches of the exemplified juice drinks.

EXAMPLE 3

Fortified Juice Drinks

| INGREDIENT | Weight | Weight | Weight | Weight |
|---|---|---|---|---|
| Water | Q.S. | Q.S. | Q.S. | Q.S. |
| Whey Protein | 8.73 kg | 8.73 kg | 8.73 kg | 8.73 kg |
| Juice concentrate 65-85% solids | 52.5 kg | 52.5 kg | 52.5 kg | 52.5 kg |
| Gamma Cyclodextrin (wt/wt %) | 0.3% | 1.5% | 2.5% | 5% |
| Dextrose | 25.3 kg | 25.3 kg | 25.3 kg | 25.3 kg |
| Sucrose | 45.0 kg | 45.0 kg | 45.0 kg | 45.0 kg |
| Fructose | 24.0 kg | 24.0 kg | 24.0 kg | 24.0 kg |
| Flavor | ~1 kg | ~1 kg | ~1 kg | ~1 kg |
| Ascorbic Acid | 0.625 kg | 0.625 kg | 0.625 kg | 0.625 kg |
| Water soluble vitamin premix | 0.238 kg | 0.238 kg | 0.238 kg | 0.238 kg |
| Citric acid | 5.0 kg | 5.0 kg | 5.0 kg | 5.0 kg |
| Milk Minerals, i.e. Ca & P salts | 4.23 kg | 4.23 kg | 4.23 kg | 4.23 kg |

The fortified juice drink is prepared by heating an appropriate amount of water to 130-140° F., and adding to it fructose, citric acid, whey protein, juice concentrate, gamma-cyclodextrin, dextrose, and sucrose and mix in liquifier, cool and add water soluble vitamin premix, flavor, ascorbic acid, and calcium and phosphorous salts. The resulting combination is subjected to HTST at 200-230° F. for approximately 5 seconds, and then hot filled into glass containers at 190° F., sealed, cooled, and labeled.

Example 4

This example illustrates a method of the present invention directed to the use of nutritional products as solid nutritional bars. As described in the following table, each exemplified formula for use in the method is prepared from a 50 kg batch, and all ingredient amounts listed in the table are recited as kg per 50 kg batch size.

EXAMPLE 4

Solid Nutritional Bar (Chocolate Flavor)

| Ingredients | Example 4.2 | Example 4.2 | Example 4.3 | Example 4.4 |
|---|---|---|---|---|
| Soy Protein Isolate | 7.51 | 7.51 | 7.51 | 7.51 |
| 42 DE corn syrup | 14.035 | 13.785 | 12.785 | 11.785 |
| High Fructose Corn Syrup 90% | 4 | 4 | 4 | 4 |
| Canola Oil | 1 | 1 | 1 | 1 |
| Fructose | 10.00 | 9.75 | 8.75 | 7.75 |
| Gamma Cyclodextrin | 0.5 | 1 | 3 | 5 |
| Vanilla flavor | 0.105 | 0.105 | 0.105 | 0.105 |
| Tricalcium Phosphate | 0.85 | 0.85 | 0.85 | 0.85 |
| Vitamin Premix | 0.25 | 0.25 | 0.25 | 0.25 |
| Alkalized Cocoa, 11% fat | 2.75 | 2.75 | 2.75 | 2.75 |
| No Sugar Added Chocolate Flavored Coating | 9 | 9 | 9 | 9 |
| Total | 50.00 | 50.00 | 50.00 | 50.00 |

Solid Nutritional Bar (Lemon Flavor)

| Ingredients | Example 4.5 | Example 4.6 | Example 4.7 | Example 4.8 |
|---|---|---|---|---|
| Fructose | 4.95 | 5 | 5 | 5 |
| Soy Protein Isolate | 9 | 9 | 9 | 9 |
| 42 DE Corn Syrup | 9.4 | 9.4 | 9.4 | 9.4 |
| Canola Oil | 1 | 1 | 1 | 1 |
| Gamma Cyclodextrin | 0.5 | 1 | 3 | 5 |
| Fructooligosaccharide Powder | 1 | 1 | 1 | 1 |
| Maltodextrin | 0 | 0.45 | 2.45 | 4.45 |
| No sugar added yogurt flavored coating | 8.5 | 8.5 | 8.5 | 8.5 |
| High fructose corn syrup, 90% | 4 | 4 | 4 | 4 |
| Glycerin, USP 99.7 | 1 | 1 | 1 | 1 |
| Vanilla flavor | 0.1 | 0.1 | 0.1 | 0.1 |
| Lemon Flavor | 0.45 | 0.45 | 0.45 | 0.45 |
| Vitamin/mineral premix | 0.25 | 0.25 | 0.25 | 0.25 |
| Tricalcium phosphate | 0.85 | 0.85 | 0.85 | 0.85 |
| Total | 50 | 50 | 50 | 50 |

The exemplified nutrition bars can be prepared by any of a number of known methods for preparing solid matrix nutrition bars, including those methods described in U.S. Pat. No. 4,496,606 (Michnowski) and U.S. Pat. No. 5,545,414 (Behr et al.), which descriptions are incorporated herein by reference.

Each of the exemplified bar formulations are manufactured using cold extrusion technology as is known and commonly practiced in the bar manufacturing art. To prepare such compositions, typically all of the powdered components are dry blended together, which typically includes the proteins, vitamin premixes, carbohydrates including gamma-cyclodextrin, etc. The fat soluble components are then blended together and mixed with any powdered premixes. Finally any liquid components are then mixed into the composition, forming a plastic like composition or dough. The resulting plastic mass can then be shaped, without further physical or chemical changes occurring, by cold forming or extrusion, wherein the plastic mass is forced at relatively low pressure through a die, which confers the desired shape. The resultant exudate is then cut off at an appropriate position to give products of the desired weight (e.g., 50 g bars). If desired the solid product is then coated with chocolate or other confectionary material, to enhance palatability, and packaged for distribution.

EXPERIMENT

I. Animal Study

The objective of the animal study was to evaluate the postprandial glycemic response of male fatty Zucker fa/fa rats to a carbohydrate challenge consisting of gamma-cyclodextrin or maltodextrin.

Twenty male fatty Zucker fa/fa rats were obtained from Harlan (Indianapolis, Ind., USA). At the time of testing, rats weighed ~450 grams. Rats were individually housed in microisolator cages on dry bedding and were given ad libitum access to water and non-purified rat diet (pelletted; 8640 Harlan Teklad 22/5 Rodent Diet; Harlan Teklad, Madison, Wis., USA). The housing facility was maintained at 19-23° C., 30-70% relative humidity, and 12-hour light-dark cycle.

Test carbohydrates were evaluated in a randomized crossover design with a 7-day washout period between each meal glucose tolerance test (MGTT). Every rat received each treatment. Rats were routinely fed the non-purified diet. After overnight food deprivation, rats were orally fed test meals as a solution. Rats consumed the test meal within 1 minute. Blood samples were collected from the tail vein and immediately analyzed for plasma glucose by the glucose oxidase method utilizing a Precision G Blood Glucose Testing System (Medisense, Inc., Bedford, Mass., USA) before (0 minutes) and 30, 60, 90, 120, and 180 minutes postprandial. Rats had free access to water throughout the MGTT.

Lodex 15® (maltodextrin) was obtained from Cerestar USA (Hammond, Ind., USA) with a dextrose equivalence (DE) of 15. Gamma-cyclodextrin (Wacker Cavamax W8) was obtained from Wacker Biochem Corp., Müchen, Germany. Carbohydrates were made into 500 g/L solutions with water. Each solution was heated in a microwave for 30 seconds to completely solubilize the carbohydrate solutions 1 hour before testing. Test meal volume was ~1 mL and was adjusted such that each rat was delivered an equivalent carbohydrate challenge (1.0 g/kg body weight).

Animal Study Results

The data representing the postprandial glycemic response of the 20 male fatty Zucker fa/fa rats fed 1.0 g/kg body weight of Lodex 15® (maltodextrin) or gamma-cyclodextrin is set forth in the following tables and in the graph illustrated in FIG. 1.

Plasma glucose response of male zucker rats fed gamma-cyclodextrin or Lodex 15

| Treatment | Avg weight (g) | 0 min | 30 min | 60 min | 90 min (mg/dl) | 120 min | 180 min |
|---|---|---|---|---|---|---|---|
| Gamma-Cyclodextrin | 459.1 ± 7.6 | 113.6 ± 4.2 | 165.6 ± 10.6 | 161.8 ± 7.8 | 151.6 ± 7.0 | 153.1 ± 6.5 | 142.6 ± 6.4 |
| Lodex 15 | 445.2 ± 25.1 | 106.1 ± 6.7 | 181.3 ± 11.3 | 209.0 ± 13.1 | 193.6 ± 12.7 | 168.2 ± 11.2 | 140.5 ± 9.4 |

| Treatment | Avg weight (g) | Change @ 0 min | Change @ 30 min | Change @ 60 min | Change @ 90 min | Change @ 120 min | Change @ 180 min |
|---|---|---|---|---|---|---|---|
| Change from baseline in plasma glucose of male zucker rats fed gamma-cyclodextrin or Lodex 15 | | | | | (mg/dl) | | |
| Gamma-Cyclodextrin | 459.1 ± 7.6 | 0 | 52.0 ± 9.4 | 48.1 ± 5.5 | 38.0 ± 4.1 | 39.4 ± 4.3 | 28.9 ± 5.3 |
| Lodex 15 | 445.2 ± 25.1 | 0 | 68.9 ± 3.4 | 111.2 ± 8.4 | 92.4 ± 6.3 | 64.6 ± 6.4 | 35.0 ± 6.1 |

The data from this particular animal study shows that oral administration of gamma-cyclodextrin in the subject animals resulted in a blunted glycemic response relative to the oral administration of a comparable amount of a linear maltodextrin, Lodex 15. For example, the data as set forth in the table and illustrated in FIG. 1 show that the glucose concentration was lower (P <0.05) at 60 and 90 minutes when rats consumed gamma-cyclodextrin as compared to the consumption of maltodextrin. These data was especially interesting given that this blunted glycemic response was noticed even after cooking or heat treatment of the gamma-cyclodextrin.

II. Human Study

The purpose of this study was to evaluate in humans the postprandial glycemic response of gamma-cyclodextrin relative to maltodextrin (Lodex® 15) and to discern whether gamma-cyclodextrin is a carbohydrate that attenuates postprandial glycemia that then could potentially serve as a low glycemic index carbohydrate.

Thirty-two healthy adult subjects received two treatments in a double-masked, randomized, crossover design. The two treatments consisted of 50 g challenges of either maltodextrin or gamma-cyclodextrin. Blood samples were collected over a three-hour period, and breath samples collected over an eight-hour period following consumption of each carbohydrate. Gamma-cyclodextrin significantly reduced plasma glucose and serum insulin area under the curve (AUC). Plasma glucose was significantly different at 15, 30, 45, 60, 150, and 180 minutes postprandially and serum insulin was significantly different at 15, 30, 45, 150, and 180 minutes postprandially between the two treatments. Breath hydrogen was significantly higher at 3 hours after gamma-cyclodextrin compared to maltodextrin, but this increase is not clinically relevant.

The results of this study indicate that consumption of gamma-cyclodextrin can lower postprandial glycemia and insulinemia compared to maltodextrin, without resulting in significant carbohydrate malabsorption.

1. Research Questions

The primary variable for this study is change from baseline for peak capillary plasma glucose concentration. Secondary variables include change from baseline for peak serum insulin concentration; positive incremental area under the curve (AUC) for insulin and glucose; plasma glucose and serum insulin concentrations at individual time points; relative glycemic response; incremental change from baseline in plasma glucose and serum insulin concentrations at individual time points; stool frequency and consistency; intensity and frequency of nausea, abdominal cramping, distention, and flatulence; and incidence of a positive breath hydrogen test. Supportive variables include breath hydrogen concentrations at individual time points, time to peak glucose and insulin concentrations, demographic and anthropometric variables (age, gender, weight, and BMI), and screen fasting capillary plasma glucose concentration.

The hypotheses for this study can be stated in terms of the primary variable, which is the change from baseline for peak capillary plasma glucose concentration ($V_p$) for the two study feeding regimens, maltodextrin (MD) ($C_1$) and gamma-cyclodextrin ($C_2$) as:

$$H_0: C_1 = C_2$$

$$H_A: C_1 \neq C_2$$

If the null hypothesis is rejected, then the alternative hypothesis that the two feedings are different with respect to the primary variable, is accepted.

2. Research Design

This study utilized a randomized, double-masked, crossover design, with a 4-14 day washout period between treatments. Before completing the two treatment visits, each subject completed one pre-study gastrointestinal tolerance test visit. Randomization was carried out by sealed envelopes stating which pre-study treatment was to be received, as well as in which sequence the two treatment visits were to be carried out. These envelopes were prepared from randomization schedules generated at Ross Products Division of Abbott Laboratories. Two product coordinators assigned an envelope from the top of the pile to each subject in the order that they passed all screening criteria and were given subject numbers.

3. Clinical Study Product

The study beverages were aqueous retort products packaged in 8 fl oz metal cans, the solid ingredients of which are described in the following table.

| Ingredients (solids) per 8 fluid ounce serving | Control | Experimental |
|---|---|---|
| Maltodextrin (Lodex 15 ®) (g) | 25 | 0 |
| Gamma-cyclodextrin (g) | 0 | 25 |
| Sodium (mg) | 52 | 52 |
| Potassium (mg) | 56 | 56 |
| Chloride (mg) | 86 | 86 |
| Vitamin C (mg) | 308 | 308 |

Besides carrying out randomization, the product coordinators were responsible for study product inventory and serving the appropriate product to subjects at each visit so that other study staff could not become aware of the study product identity. At the pre-study tolerance test visit, subjects received 8 fl oz of a study product containing either 25 g of maltodextrin or 25 g of gamma-cyclodextrin. Approximately one-third of the subjects were assigned to the maltodextrin treatment and two-thirds to the gamma-cyclodextrin treatment. At each of the two treatment visits, subjects received 16 fl oz of a study product containing either 50 g of maltodextrin or 50 g of gamma-cyclodextrin. All beverages were served cold in styrofoam cups with lids and straws, labeled only with the subject number, subject initials and visit number, with the intention of hiding any slight differences in appearance that could be visible to study staff or subjects.

The 25 g carbohydrate dose was fed to subjects at the pre-study tolerance test visit in order to elucidate whether or not the study product was tolerated before a larger dose was given at the subsequent treatment visits. The 50 g carbohydrate dose was chosen for each of the treatment visits because this is the carbohydrate load used in certain published glycemic response studies, and is also a common carbohydrate dose utilized in determining glycemic indices.

4. Subjects

At least 28 subjects (14 in each treatment arm) were needed to detect, with 85% power, a 15% difference in the means between products with respect to the primary variable. Power analysis was done using nQuery-Advisor® Release 4.0. It was also determined that 34 subjects should be randomized into the study in order to obtain requisite 28 evaluable subjects.

Subject eligibility criteria were as follows:

Subject is between 18 and 75 years of age

Subject is male, or non-pregnant female greater than six weeks postpartum and non-lactating Subject has a body mass index (BMI) of 18-28 kg/m$^2$, or $\leq$30 kg/m$^2$ if waist circumference is $\leq$35 inches if female and $\leq$40 inches if male (citation!)

Subject is free from active metabolic or gastrointestinal diseases that may interfere with nutrient absorption, distribution, metabolism, or excretion Subject does not use tobacco products Subject does not have diabetes mellitus or impaired glucose tolerance (screen fasting capillary plasma glucose $\geq$110 mg/dl) (cite)

Subject does not have clotting or bleeding disorders

Subject has not had an infection (requiring medication or hospitalization), surgery, or corticosteroid treatment in the last 3 months, or antibiotics in the last 3 weeks Subject is taking daily medications (acetaminophen, salicylates, thiazide diuretics, steroids, etc.) or dietary supplements at doses that would interfere with nutrient absorption, metabolism, excretion, or gastric motility Subject is not allergic to heparin, nuts, dairy products, corn products, sucrose, cow's milk, soy products, or vanilla flavorings Subject has not fainted or experienced other adverse reactions in response to blood collection prior to enrollment into this study Subject is a hydrogen producer or produces more methane than hydrogen Subject has voluntarily signed and dated informed consent form 5. Procedures Subjects participating in this study came to the study site on six separate occasions. Each completed a screening visit, a breath hydrogen and fasting plasma glucose screening visit, a pre-study tolerance test visit, two treatment visits, and an exit visit.

6. Screening Visit

At the screening visit, subjects read and signed an informed consent form; became familiarized with the study procedures; completed a screening questionnaire; took a pregnancy test if female (Fact Plus® Select one-step urinary pregnancy test, Abbott Laboratories, Columbus, Ohio); had height and weight measured; and taste tested Ensure® products to determine flavor preferences for pre-treatment and post-treatment meals. Subjects meeting all eligibility requirements at this screening visit were scheduled for a breath-hydrogen and fasting plasma glucose screening visit.

7. Breath Hydrogen, Fasting Plasma Glucose Screening Visit

On the day before this visit, subjects stopped consuming food and beverages other than water after 4:00 p.m. Between 4-9:00 p.m., subjects consumed a low-residue meal consisting of 8 fluid ounces of Ensure® Plus liquid formula (chocolate, strawberry, or vanilla) as well as a variable number of Ensure® Nutrition and Energy Bars (Chewy Chocolate Peanut, Chocolate Maple, Cinnamon Oat 'n Raisin, or Cookies 'n Cream) to equal approximately one-third of the subject's daily caloric requirements as determined by the Harris-Benedict equation multiplied by an activity factor of 1.3. Subjects consumed the same flavor and quantity of beverage and bars before this visit and the two treatment visits. They also consumed the same flavor beverage after each of the two treatment visits. After 9:00 p.m. the night before the visit, subjects consumed no food or beverage except water. The total fasting time before the visit was between 10 and 16 hours.

The morning of the breath hydrogen and fasting plasma glucose screening visit, subjects reported to the study cite. They provided a fasting breath sample using the QuinTron Easy Sampler device (QuinTron Instrument Company, Milwaukee, Wis.) to collect 10 mL of alveolar air, and then consumed 10 grams of lactulose (Kristalose, Bertek Pharmaceuticals, Sugar Land, Tex.) in approximately 8 fl oz of water. Subjects then resumed fasting and collected breath samples at 1, 2, 3, and 4 ($\pm$10 minutes) hours after the time in which they began consuming the lactulose solution. Subjects were allowed to leave the study site after the lactulose was consumed and continue to collect breath samples on their own. When subjects returned the breath samples, hydrogen and methane were analyzed via gas chromatography. Subjects producing hydrogen, and less methane than hydrogen, were then randomized to receive one of the two pre-study test beverages, as well as to one of two treatment arms.

8. Pre-Study Gastrointestinal Tolerance Test Visit

For the pre-study tolerance test, subjects were instructed to not consume anything the day before that was known by them to cause gastrointestinal symptoms. They also completed an overnight 10-16 hour fast. The morning of the test visit, subjects reported to the study site and consumed 8 fl oz of one of the two study beverages within 10 minutes. The study beverage contained either 25 grams of maltodextrin or 25 grams of gamma-cyclodextrin. Subjects then resumed fasting. Subjects were allowed to leave the study site after the beverage had been consumed, however they were instructed to remain fasting for three hours from the time they began drinking the beverage. Subjects recorded gastrointestinal tolerance symptoms and stool frequency and consistency for 24 hours from the time they began drinking the study beverage.

Upon subject completion of the gastrointestinal tolerance symptoms and stool frequency and consistency forms, the data were reviewed for signs of abnormal tolerance by a physician. The purpose of this symptom review was to determine if the product was generally well-tolerated. Because there were no significant differences in gastrointestinal tolerance between 25 grams of gamma-cyclodextrin and 25 grams of maltodextrin as determined by the reviewing physician, the study continued and subjects were scheduled for two treatment visits.

9. Treatment Visits

On two separate treatment visits, subjects received, in random order, one of the two study beverages. Three days prior to each treatment visit, subjects recorded their food and beverage intake in a food diary. Subjects were required to consume $\geq$150 g of carbohydrate each day for three days prior to each treatment. Subjects were not to engage in vigorous exercise for 24 hours before each treatment. Subjects consumed an evening low residue Ensure® meal and completed a 10-16 hour overnight fast as detailed previously.

The morning of each treatment, subjects consumed 4-6 fl oz of water upon waking. Subjects arrived at the study site between 7-7:30 a.m. and rested for 30 minutes. During this time, a member of the study staff looked over each subject's food records, and interviewed them about any medication changes or adverse symptoms they had experienced since their last visit, as well as if they have exercised in the previous 24 hours. If the subject failed to consume at least 150 grams of carbohydrate on each of the previous three days, or failed to refrain from exercise within the past 24 hours, the subject's treatment was rescheduled. Upon completing the 30-minute rest period, the subject's weight, blood pressure, temperature, heart rate, and respiratory rate was measured.

After vital signs were collected and found to be within acceptable ranges as specified by the study physician, a nurse inserted an indwelling catheter in the subject's arm and collected a baseline venous blood sample of no more than 10 mL for the measurement of insulin. A blood sample (1 drop) was also obtained via capillary finger-stick for measurement of plasma glucose. A breath sample was collected for measurement of breath hydrogen.

Upon completion of baseline samples, the subject proceeded to the study site and consumed 16 fl oz of one of the two test beverages in no more than 10 minutes. After consumption of the study beverage, the subject resumed fasting. Time 0 was designated as the time at which the subject began drinking the study beverage. Additional venous blood samples and capillary plasma glucose finger sticks were collected at 15, 30, 45, 60, 90, 120, 150, and 180 (±5) minutes after the start of the study beverage. Additional breath samples were collected at 1, 2, 3, 4, 5, 6, 7, and 8 (±10 minutes) hours postprandially. Subjects were limited to the consumption of 8 fl oz of water during this three hour blood collection period. Approximately 10 mL of normal saline was injected into the vein after each blood draw in order to keep the line open and to replace the fluid lost from the blood collected.

After the 180-minute blood and breath samples were collected, the subject was allowed to leave the study site and collect the remaining breath samples (hours 4-8) on their own. During the remainder of the breath collection period, the subject was instructed to refrain from sleep and exercise. Subjects were to remain fasting with the exception of an optional one or two 8 fl oz cans of Ensure® Plus. The flavor given to each subject was the same as that which was chosen for the pre-treatment meals, and the number of cans chosen remained constant for both treatments. Subjects were allowed to consume water as desired during this time. After completion of breath sample collection, subjects were free to resume their normal sleeping, eating, and exercise patterns. They continued to record gastrointestinal symptoms, stool frequency and consistency, and medication usage for the next 48 hours. At their next study visit, subjects returned their breath sample tubes, breath sample data collection form, medication form, stool frequency and consistency forms, and gastrointestinal tolerance forms.

10. Exit Visit

Subjects returned no earlier than 48 hours and no later than 7 days after their last treatment visit for an exit visit. At this visit the subject was interviewed about any adverse symptoms they had experienced since their last treatment. They returned the breath sample tubes, breath sample data collection form, medication form, stool frequency and consistency forms, and gastrointestinal tolerance forms from their second treatment.

11. Glucose Analysis

Plasma glucose was measured using an AccuChek Advantage Blood Glucose Monitoring System® (Roche Diagnostics, Indianapolis, Ind.). This system measures glucose in whole blood but is calibrated to plasma glucose. The accuracy of the AccuChek® meter was tested in a previous study, and it was found to correlate well with the YSI glucose analyzer. The YSI glucose analyzer uses the glucose oxidase method for evaluating blood glucose and is commonly used in glycemic response studies. Positive incremental area under the plasma glucose response curve for two hours after each treatment will be calculated using the method of Wolever et al, *The glycemic index: methodology and clinical implications*, Amer. J. Clin. Nutr. 1991, 54, 846-854.

12. Insulin Analysis

Insulin was analyzed using DSL-10-1600 Insulin ELISA Kits (Diagnostic Systems Laboratories, Inc, Webster, Tex.). Enzyme-linked immunosorbent assay (ELISA) works by incubating insulin standards, controls, and unknowns with an anti-insulin antibody in microtitration wells also containing anti-insulin antibodies adhered to the bottom of the wells. After incubation, a "sandwich" is formed with the insulin molecule between two antibodies, one of which is attached to the well. Each well is then incubated with tetramethylbenzidine (TMB), which, upon interaction with the insulin-antibody complex, results in a color change. An acidic stopping solution is then added and the enzymatic turnover of TMB is determined by dual wavelength absorbance measurement at 450 and 620 nanometers. The log absorbance is proportional to the concentration of insulin present. The standard insulin solutions are used to create a standard plot, and control insulin solutions used to check the accuracy of the plot.

13. Breath Hydrogen Analysis

Breath hydrogen was analyzed to determine if the carbohydrate in the study product had been malabsorbed. Analysis was done using the QuinTron Microlyzer Model SC gas chromatograph (QuinTron Instrument Company, Milwaukee, Wis.) for carbon dioxide, methane and hydrogen. Observed hydrogen and methane values were corrected for atmospheric contamination of alveolar air by normalization of the observed $CO_2$ to 40 mm Hg (5.3 kPa), which is the partial pressure of $CO_2$ in alveolar air. An observed $CO_2$ value must be greater than or equal to 1.5 ppm in order for the breath sample to be considered usable. Any value less than this indicates that the sample did not contain a sufficient quantity of alveolar air. Values of corrected $H_2$ that are 10 ppm or greater above the basal nadir value are indicative of carbohydrate malabsorption according to the criteria outlined by Strocchi et al., *Detection of malabsorption of low doses of carbohydrate: accuracy of various breath $H_2$ criteria*, Gastroenterology 1993, 105, 1404-1410.

To be eligible to participate in this study, subjects were required to be hydrogen producers, and also to produce more hydrogen than methane. Subjects were considered to be hydrogen producers if they exhibited $\geq 10$ ppm increase in breath hydrogen from the basal nadir value within four hours after ingestion of 10 grams of lactulose, a nondigestible carbohydrate. Subjects were considered to produce more hydrogen than methane if the positive incremental AUC over the four hour test was greater for hydrogen than for that of methane.

14. Gastrointestinal Tolerance Analysis

Subjective records of gastrointestinal symptoms and stool frequency and consistency were kept by the subjects for the pre-study gastrointestinal tolerance test and each of the two treatment visits. Subjects marked a single slash through a 10 cm horizontal line to indicate the intensity (0 representing "Absent" and 10 representing "Severe") and frequency (0 representing "Usual" and 10 representing "More than Usual") of nausea, abdominal cramping, distention and flatulence. Stool consistency was rated for each bowel movement on a scale of 1 to 5 (1=watery, 5=hard).

15. Statistical Analysis

Descriptive statistics were calculated for the following variables: change from baseline for peak capillary plasma glucose, serum insulin, and breath hydrogen concentrations; positive incremental AUC for plasma glucose and serum insulin; plasma glucose and serum insulin concentrations at individual time points; relative glycemic response; relative insulinemic response; incremental change from baseline in plasma glucose and serum insulin concentrations at individual time points; the intensity and frequency of nausea, abdominal cramping, distention, and flatulence; stool frequency and consistency; and demographic and anthropometric variables of age, weight, BMI, and screen fasting plasma glucose.

The Shapiro-Wilk test was done to assess normality of the data, and transformations were attempted to increase normality of non-normally distributed data. The NCSS module for cross-over designs (Version 4, 2001, Kaysville, Utah) was used to analyze treatment, period, and carryover effects for the following variables: change from baseline for peak capillary plasma glucose and serum insulin concentrations, and positive incremental AUC for plasma glucose and serum insulin. Analysis of variance (ANOVA) was done to determine if there were differences in plasma glucose and serum insulin concentrations at individual time points. If there is a significant period or carryover effect ($p<0.10$), only first period data will be used to determine if there is a significant difference between treatments. Besides the determination of period and carryover effects, all other data will be deemed significantly different only if $p<0.05$.

16. Clinical Study Results

Thirty five (35) subjects met all eligibility criteria and were thus randomized into the study. Of these subjects, 32 completed all study visits and were deemed evaluable for statistical analysis purposes. All three subjects that exited from the study prematurely did so after the gastrointestinal tolerance test visit and before the first treatment visit. One female began taking antibiotics and therefore no longer met eligibility criteria, one male exited when he learned of possible difficulties in receiving payment because of his visa status, and one male was lost to follow up. The 32 evaluable subjects had a mean age of 24.97±0.64 y, mean weight of 67.8±2.0 kg, mean BMI of 23.2±0.3 kg/m$^2$, and mean fasting plasma glucose of 4.73±0.10 mmol/L.

Statistical analysis was done using evaluable subjects. All data were tested for normality using the Shapiro-Wilk test. Only glucose AUC data was deemed normally distributed according to this test. Data transformations were then attempted in order to normalize data. A square root transformation normalized insulin AUC and adjusted peak insulin data, so statistical analysis was run on the transformed data for these two data sets. For all other data, transformations of square root, log, ln, sin, 1/x, and rank did not result in normality. In this case, statistical analysis was done on the raw data and the most visually normal transformation, and these two analyses were compared. In most cases, the two analyses did not differ in their assessment of statistical significance. If they did differ in their analysis of significance, no significant difference is reported. If the level of significance was different, the more conservative p-value is reported. Crossover analysis was done to determine differences in glucose and insulin AUC, adjusted peak glucose and insulin, and intensity and frequency of nausea. No significant period or carryover effects were found on any of these data. General linear model ANOVA was done to determine if there were differences between treatments for plasma glucose, serum insulin, and breath hydrogen at individual time points, and to determine if there were significant effects of subject, time, treatment, or time-treatment interaction.

17. Plasma Glucose Response

Figure 2:
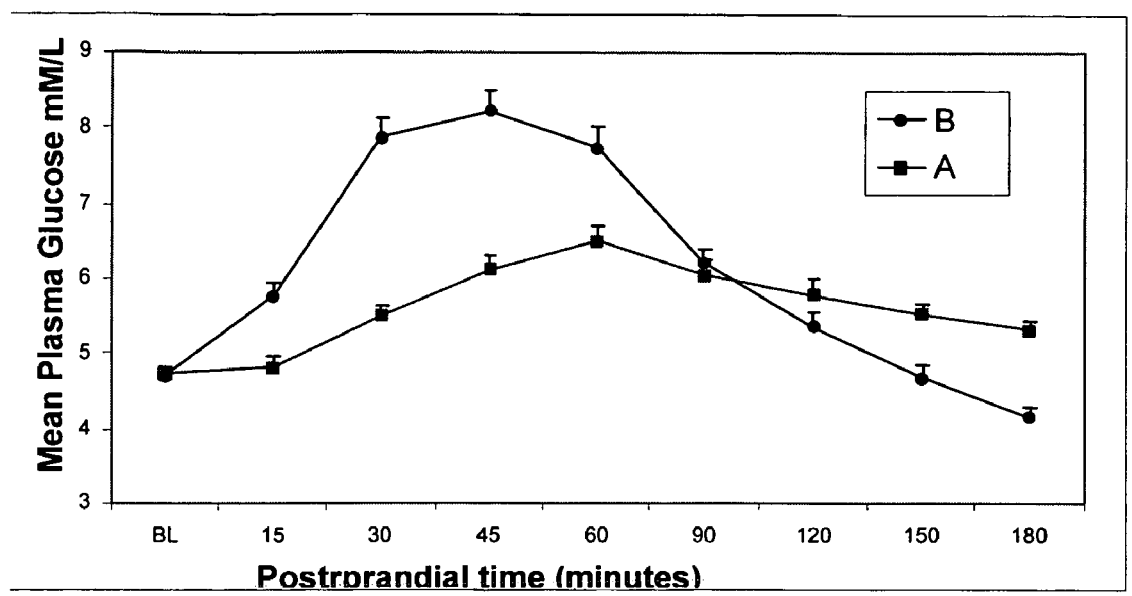
FIG. 2 is a graph illustrating the postprandial plasma glucose responses obtained in human subjects as reported in the clinical study described herein. Plasma glucose concentrations for the gamma-cyclodextrin group (A) and for the maltodextrin group (B) are plotted at individual time points. Values represent mean±SEM, n=31-32.

Postprandial plasma glucose responses from the clinical study are illustrated in the FIG. 2 graph, wherein plasma glucose concentrations for gamma-cyclodextrin (A) and maltodextrin (B) are plotted at individual time points. Values represent mean±SEM, n=31-32.

Figure 3:
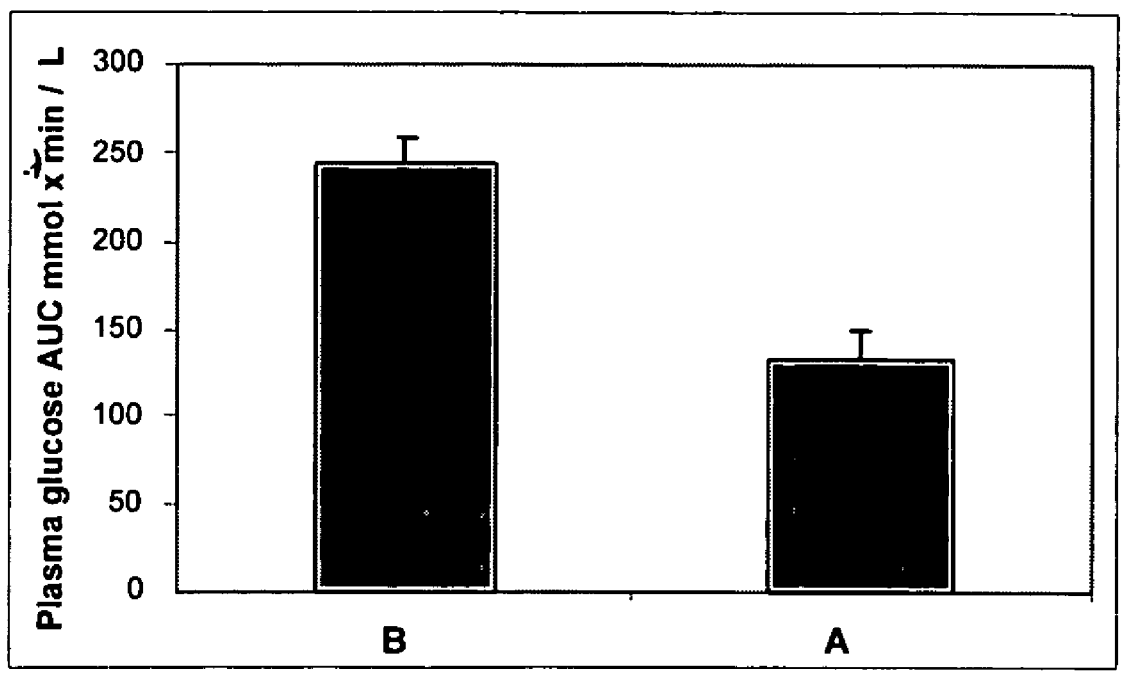
FIG. 3 is a chart illustrating the postprandial plasma glucose response obtained in human subjects as reported in the clinical study described herein, wherein the response is measured as positive incremental 120 minute plasma glucose AUC values for the gamma cyclodextrin group (A) and for the maltodextrin group (B). Values represent mean±SEM, n=31.

The plasmas glucose response from the study is also illustrated in the FIG. 3 chart showing the postprandial plasma glucose response in the human subjects, wherein the response is measured as positive incremental 120 minute plasma glucose AUC values for gamma cyclodextrin (A) and maltodextrin (B). Values represent mean±SEM, n=31.

There were no significant differences between treatments for baseline plasma glucose. Crossover analysis indicated a significant difference between the two treatments with regard to the primary variable, adjusted peak glucose ($p<0.0001$). Analysis of variance revealed a significant difference in plasma glucose between treatments at 15, 30, 45, 60, 150, and 180 minutes ($p<0.001$ at 60 min, $p<0.0001$ at 15, 30, 45, 150, and 180 min) (see FIG. 2). Positive incremental 120 min AUC was significantly different between the two treatments ($p<0.0001$), with maltodextrin having a value of 242.8±15.2 and gamma-cyclodextrin having a value of 133.2±16.5 (see FIG. 3). The relative glycemic response of gamma-cyclodextrin compared with maltodextrin from baseline to 120 min was 55%.

2. Serum Insulin

Figure 4:
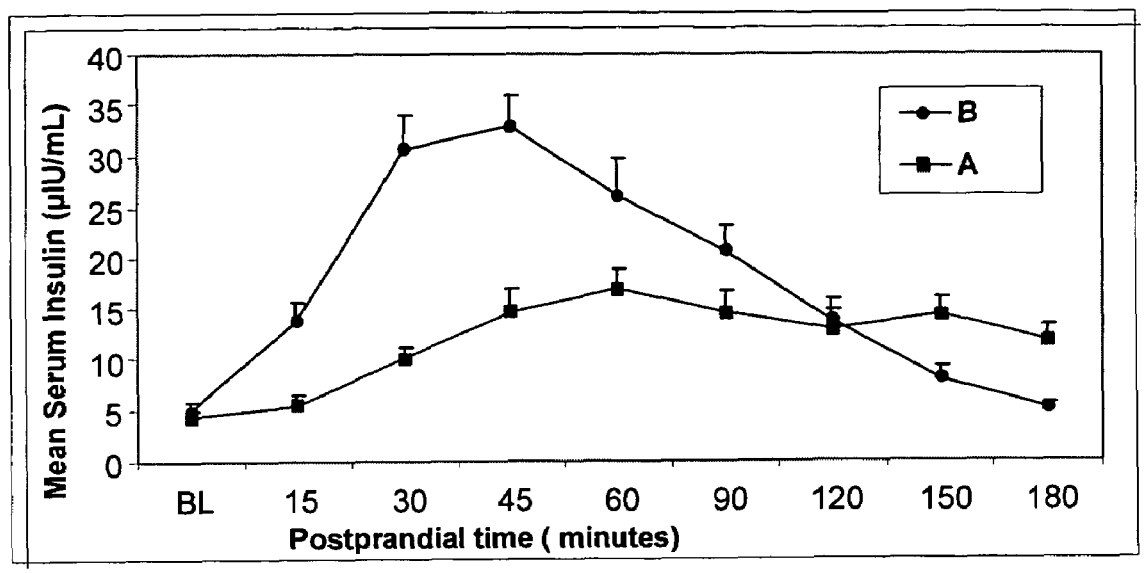
FIG. 4 is a graph illustrating postprandial serum insulin concentrations obtained in human subjects as reported in the clinical study described herein, wherein the concentrations for the maltodextrin group (B) and for the gamma-cyclodextrin group (A) are plotted at individual time points. Values represent mean±SEM, n=29-42.

Postprandial plasma insulin responses from the clinical study are illustrated FIG. 4, wherein serum insulin concentrations for the gamma-cyclodextrin (A) and maltodextrin (B) groups are plotted at individual time points. Values represent mean±SEM, n=29-32.

Figure 5:
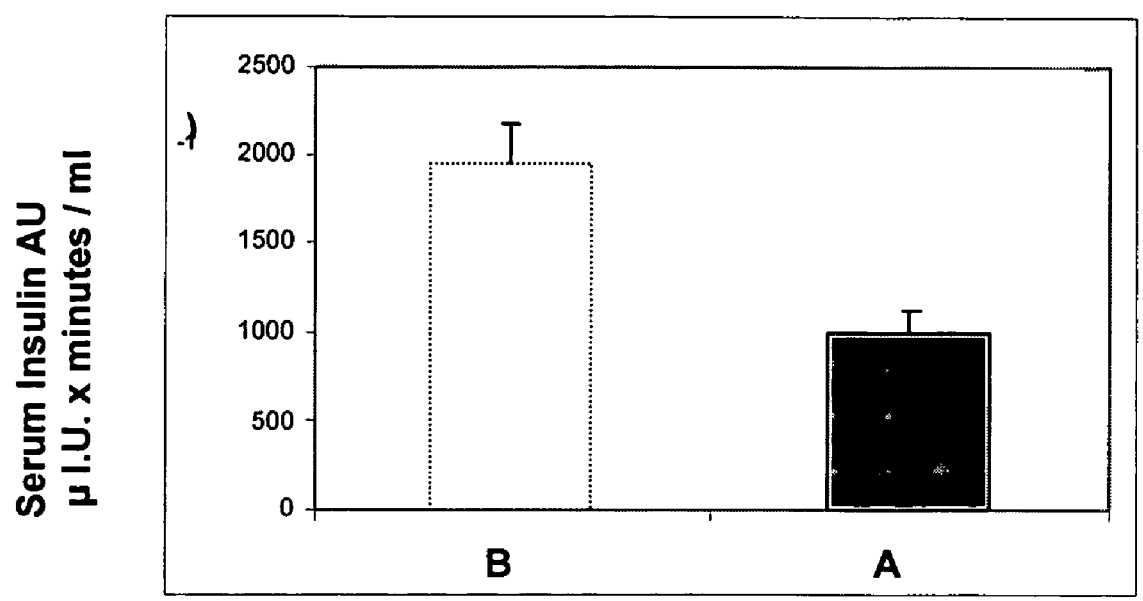
FIG. 5 is a chart illustrating the serum insulin responses obtained in human subjects as reported in the clinical study described herein, wherein the values are positive incremental 120 minute serum insulin AUC values for the maltodextrin group (B) and for the gamma-cyclodextrin group (A). Values represent mean±SEM, n=27 for maltodextrin and n=31 for gamma-cyclodextrin.

Post prandial plasma insulin responses from the clinical study are also illustrated in FIG. 5, wherein serum insulin is measured as positive incremental 120 minute serum insulin AUC values for the gamma cyclodextrin (A) and maltodextrin (B) groups. Values represent a mean±SEM, n=27 for malotodextrin and 31 for gamma-cyclodextrin.

No significant differences were found between treatments for baseline serum insulin. The adjusted peak insulin value was significantly decreased with gamma-cyclodextrin compared with maltodextrin ($p=0.0003$). Insulin values between the two treatments were found to be significantly different at 15 min ($p=0.001$), 30 min ($p=0.0007$), 45 min ($p=0.0003$), 150 min ($p=0.0007$) and 180 min ($p=0.0002$) (see FIG. 4). Positive incremental 120 min AUC was significantly different between the two treatments ($p=0.0006$), with maltodextrin having a value of 1951.8±222.3 and gamma-cyclodextrin having a value of 993.4±131.6 (see FIG. 5). Relative insulinemic response of gamma-cyclodextrin compared to maltodextrin from baseline to 120 min was 51%.

3. Breath Hydrogen

Figure 6:
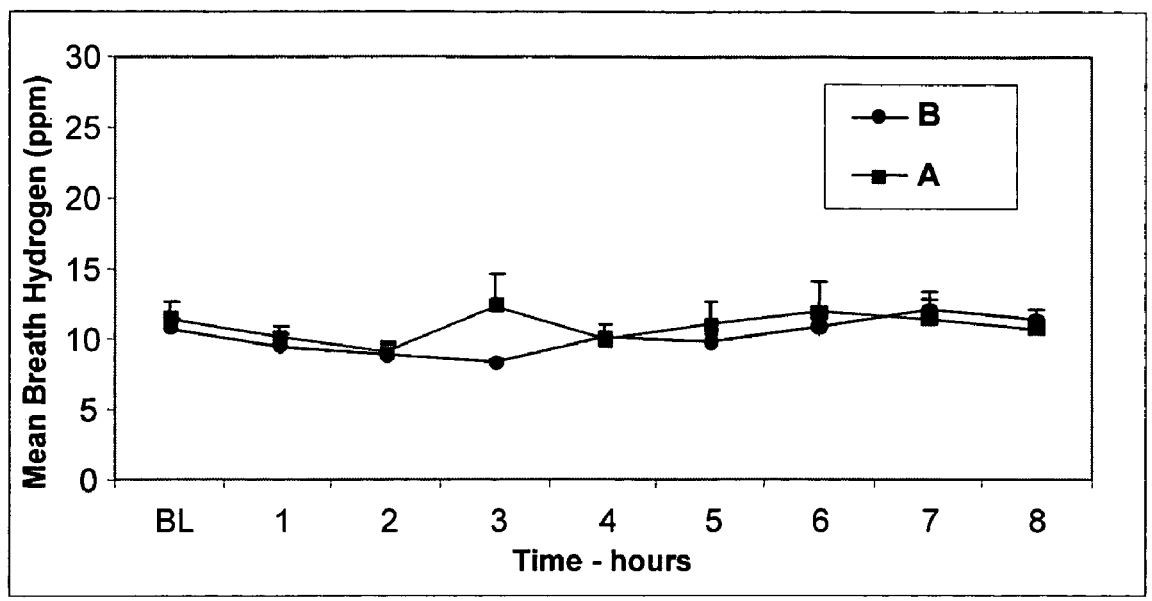
FIG. 6 is a graph illustrating breath hydrogen concentrations obtained from human subjects as reported in the clinical study described herein, wherein the concentrations are reported for the maltodextrin group (B) and the gamma-cyclodextrin group (A) at individual time points. Values represent±SEM, n=29-32.

Four of 28 evaluable subjects were classified as having a positive breath hydrogen test for the gamma-cyclodextrin treatment, whereas eight of 29 had a positive breath hydrogen test with the maltodextrin treatment. The odds ratio for positive breath hydrogen test was determined to be 0.43 (0.11-1.63), indicating no significant difference in malabsorption between the two treatments. Analysis of variance revealed a significantly higher mean breath hydrogen value for gamma-cyclodextrin only at the hour 3 time point (p=0.01) (see FIG. 6). Although significantly different, a 4 ppm difference does not have significant clinical relevance.

4. Gastrointestinal Tolerance

Figure 7:
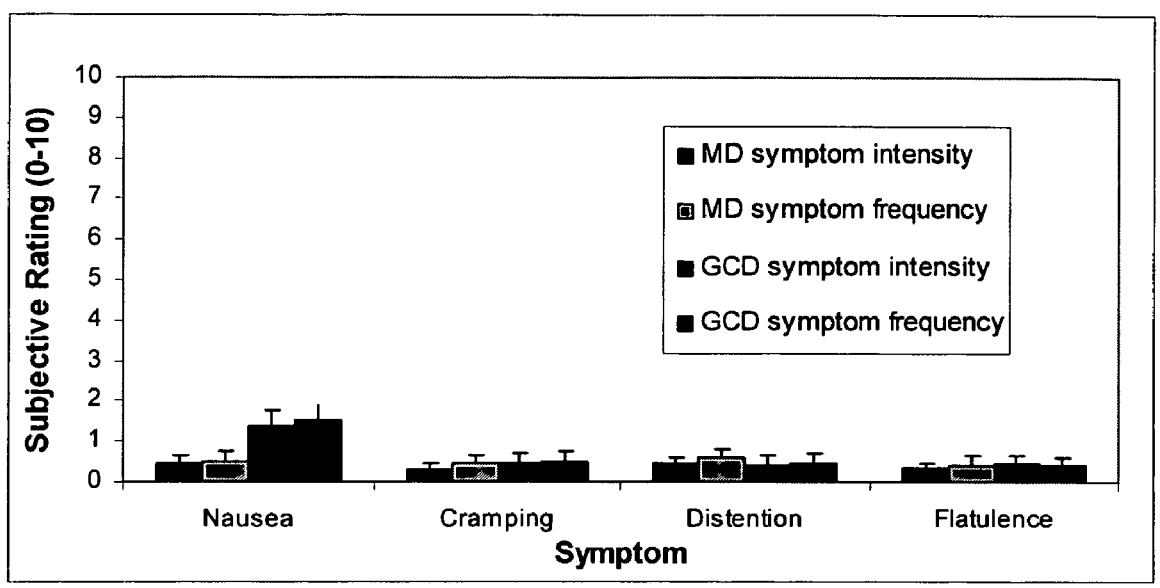
FIG. 7 is a chart illustrating intensity and frequency of gastrointestinal symptoms as reported in the clinical study during the first 24 hours after ingestion of either maltodextrin or gamma-cyclodextrin. Values represent mean±SEM, n=31-32.

Intensity and frequency of nausea during the first 24 hours after treatment was not significantly different between MD and GCD as determined by crossover analysis, however data were abnormally distributed and transformations did not improve normality. Intensity and frequency of abdominal cramping, distention, and flatulence during the first 24 hours after treatment, and intensity and frequency of all symptoms during the second 24 hours after treatment were less than 1.0 on a 10 point subjective rating scale (see FIG. 7). Intensity and frequency of nausea during the first 24 hours was the only symptom with a mean greater than 1.0. However, 1.34 and 1.50, the means for nausea intensity and frequency respectively, are not clinically significant. There were no significant differences in stool frequency and consistency between treatments.

5. Summary

The data from the study shows that positive incremental AUC from baseline to 120 minutes was significantly smaller in gamma-cyclodextrin compared to maltodextrin for both plasma glucose and serum insulin. Several individual time points over the three-hour testing period were also found to be significantly different between the two treatments. Breath hydrogen, gastrointestinal symptoms, and stool frequency and consistency were largely unaffected by the two treatments. Taken together, these data indicate that oral administration of gamma-cyclodextrin can result in reduced postprandial glycemia and insulinemia as compared to the maltodextrin control. Gamma-cyclodextrin exerts these effects without causing adverse gastrointestinal symptoms or significant malabsorption.

What is claimed is:

1. A method for producing a blunted postprandial glycemic response in a diabetic individual, said method comprising:
   preparing a nutritional product for administration to a diabetic individual by replacing high glycemic response carbohydrates in the nutritional product with gamma-cyclodextrin; and
   administering to the diabetic individual the nutritional product comprising the added gamma cyclodextrin.

2. The method of claim 1 wherein the nutritional product further comprises a component selected from the group consisting of fat, protein, carbohydrate, and combinations thereof.

3. The method claim 1 wherein the nutritional product comprises, as a percentage of total calories in the product, from about 10% to about 34% protein, from about 10% to about 40% fat, and from about 24% to 80% carbohydrate inclusive of the gamma-cyclodextrin.

4. The method of claim 1 wherein the nutritional product is a liquid beverage containing at least about 0.1% gamma-cyclodextrin by weight of the beverage.

5. The method of claim 1 wherein the nutritional product is a liquid beverage containing from about 1% to about 6% gamma-cyclodextrin by weight of the liquid beverage.

6. The method of claim 1 wherein the nutritional product is a solid product containing at least about 1% gamma-cyclodextrin by weight of the solid product.

7. The method of claim 1 wherein the nutritional product is a solid product containing from about 5% to about 10% gamma-cyclodextrin by weight of the solid product.

8. The method of claim 7 wherein the solid product is in bar form.

9. The method of claim 1 wherein the gamma-cyclodextrin represents from about 5% to 100% by weight of the total carbohydrates in the product.

10. The method of claim 1 wherein the gamma-cyclodextrin represents 100% by weight of the total carbohydrates in the product.

11. The method of claim 1 wherein the diabetic is afflicted with diabetes mellitus.

12. The method of claim 1 wherein the product is a meal replacement product.

13. The method of claim 1 wherein the product is substantially free of alpha and beta cyclodextrins.

14. A method of reducing the occurrence of nighttime hypoglycemia in a diabetic individual, said method comprising:
   preparing a nutritional product for administration to a diabetic individual by replacing high glycemic response carbohydrates in the nutritional product with gamma-cyclodextrin; and
   administering to the diabetic individual the nutritional product comprising the added gamma-cyclodextrin immediately before bedtime.

15. The method of claim 14 wherein the nutritional product further comprises a component selected from the group consisting of fat, protein, carbohydrate, or combinations thereof.

16. The method of claim 14 wherein the nutritional product comprises, as a percentage of total calories in the product, from about 10% to about 35% protein, from about 10% to about 40% fat, and from about 25% to about 80% carbohydrate inclusive of the gamma-cyclodextrin.

17. The method of claim 14 wherein the nutritional product is a liquid beverage containing at least about 0.1% gamma-cyclodextrin by weight of the beverage.

18. The method of claim 14 wherein the nutritional product is a liquid beverage containing from about 1% to about 6% gamma-cyclodextrin by weight of the liquid beverage.

19. The method of claim 14 wherein the nutritional product is solid product containing at least about 1% gamma-cyclodextrin by weight of the solid product.

20. The method of claim 14 wherein the nutritional product is a solid product containing from about 5% to about 10% gamma-cyclodextrin by weight of the solid product.

21. The method of claim 20 wherein the solid product is in bar form.

22. The method of claim 14 wherein the gamma-cyclodextrin represents from about 5% to about 100% by weight of the total carbohydrates in the product.

23. The method of claim 14 wherein the gamma-cyclodextrin represents 100% by weight of the total carbohydrates in the product.

24. The method of claim 14 wherein the product is a meal replacement product.

25. The method of claim 14 wherein the product is substantially free of alpha and beta cyclodextrins.

26. A method of providing an insulin dependent individual with nutrition while reducing postprandial insulin secretion, said method comprising:
- preparing a nutritional product for administration to an insulin dependent individual by replacing high glycemic response carbohydrates in the nutritional product with gamma-cyclodextrin; and
- administering to the insulin dependent individual the nutritional product comprising the added gamma cyclodextrin.

27. The method of claim 26 wherein the nutritional product further comprises a component selected from the group consisting of fat, protein, carbohydrate and combinations thereof.

28. The method of claim 26 wherein the nutritional product comprises, as a percentage of total calories in the product, from about 10% to about 35% protein, from about 10% to about 50% fat, and from about 25% to about 80% carbohydrate inclusive of the gamma-cyclodextrin.

29. The method of claim 26 wherein the nutritional product is a liquid beverage containing at least about 0.1% gamma-cyclodextrin by weight of the beverage.

30. The method of claim 26 wherein the nutritional product is a liquid beverage containing from about 1% to about 6% gamma-cyclodextrin by weight of the liquid beverage.

31. The method of claim 26 wherein the nutritional product is a solid product containing at least about 1% gamma-cyclodextrin by weight of the solid product.

32. The method of claim 26 wherein the nutritional product is a solid product containing from about 5% to about 10% gamma-cyclodextrin by weight of the solid product.

33. The method of claim 26 wherein the gamma-cyclodextrin represents from about 5% to 100% by weight of the total carbohydrates in the product.

34. The method of claim 26 wherein the gamma-cyclodextrin represents 100% by weight of the total carbohydrates in the product.

35. The method of claim 26 wherein the insulin dependent individual is afflicted with diabetes mellitus.

36. The method of claim 26 wherein the product is a meal replacement product.

37. The method of claim 26 wherein the product is substantially free of alpha and beta cyclodextrins.

38. A method of normalizing blood glucose levels in individuals with impaired glucose tolerance, said method comprising:
- preparing a nutritional product for administration to an individual with impaired glucose tolerance by replacing high glycemic response carbohydrates in the nutritional product with gamma-cyclodextrin; and
- administering to the individual with impaired glucose tolerance the nutritional product comprising the added gamma-cyclodextrin.

39. A method of minimizing the occurrence of reactive hypoglycemia in a non-diabetic individual susceptible to reactive hypoglycemia, said method comprising:
- preparing a nutritional product for administration to an individual susceptible to reactive hypoglycemia by replacing high glycemic response carbohydrates in the nutritional product with gamma-cyclodextrin; and
- administering to the individual susceptible to reactive hypoglycemia the nutritional product comprising the added gamma-cyclodextrin.

40. A method a normalizing blood glucose levels in an individual with gestational diabetes or impaired glucose tolerance during pregnancy, said method comprising:
- preparing a nutritional product for administration to an individual with gestational diabetes or impaired glucose tolerance during pregnancy by replacing high glycemic response carbohydrates in the nutritional product with gamma-cyclodextrin; and
- administering to the individual with gestational diabetes or impaired glucose tolerance the nutritional product comprising the added gamma-cyclodextrin.

* * * * *